(12) United States Patent
Weaver, III et al.

(10) Patent No.: US 11,780,817 B2
(45) Date of Patent: Oct. 10, 2023

(54) METHODS FOR PREPARING FAVIPIRAVIR

(71) Applicant: Weaver Labs, LLC, Stillwater, OK (US)

(72) Inventors: Jimmie Dean Weaver, III, Stillwater, OK (US); Anuradha Singh, Stillwater, OK (US)

(73) Assignee: Weaver Labs, LLC, Stillwater, OK (US)

( * ) Notice: Subject to any disclaimer, the term of this patent is extended or adjusted under 35 U.S.C. 154(b) by 0 days.

(21) Appl. No.: 17/323,910

(22) Filed: May 18, 2021

(65) Prior Publication Data
US 2021/0355090 A1 Nov. 18, 2021

Related U.S. Application Data

(60) Provisional application No. 63/026,272, filed on May 18, 2020.

(51) Int. Cl.
*C07D 241/08* (2006.01)

(52) U.S. Cl.
CPC .................................. *C07D 241/08* (2013.01)

(58) Field of Classification Search
None
See application file for complete search history.

(56) References Cited

U.S. PATENT DOCUMENTS

2018/0141920 A1* 5/2018 Uchida ................ C07D 241/24

* cited by examiner

*Primary Examiner* — Samantha L Shterengarts
(74) *Attorney, Agent, or Firm* — Polsinelli PC

(57) ABSTRACT

The present invention provides methods for preparing Favipiravir (6-fluoro-3-hydroxypyrazine-2-carboxamide).

6 Claims, 20 Drawing Sheets

METHODS FOR PREPARING FAVIPIRAVIR

CROSS-REFERENCE TO RELATED APPLICATION

This application claims benefit of U.S. Provisional Patent Application No. 63/026,272, which was filed in the U.S. Patent and Trademark Office on May 18, 2020, all of which is incorporated herein by reference in its entirety for all purposes.

FIELD OF THE INVENTION

The present disclosure generally relates to methods for preparing Favipiravir.

BACKGROUND OF THE INVENTION

Favipiravir (6-fluoro-3-hydroxypyrazine-2-carboxamide) is a small molecule that has been investigated for its antiviral properties. These investigations intensified recently in connection with the novel coronavirus (COVID-19) outbreak that began in late 2019. Trials documented in the literature reported that when 1600 mg of Favipiravir was taken for 2 days followed by 600 mg for 12 days this treatment regimen led to a lower viral load in patients suffering from COVID-19 decreasing both the time taken for patients to test negative (11 days to 4 days) and improved lung conditions as supported by X-ray.[1] Favipiravir has been used both individually and in combination with other antiviral therapeutics.[2] In another study it was shown to significantly outperform Arbidol, more effectively relieving fever and cough, with minimal and manageable side effects.[3]

For influenza, Favipiravir has been shown to function by selectively inhibiting the RNA-dependent RNA polymerase of the influenza virus.[4,5] Furthermore, it has shown inhibition of a number of other viral infections such as bunyavirus, flavivirus, arenavirus, and norovirus.[4,6,7]

What is needed are methods to prepare 6-fluoro-3-hydroxypyrazine-2-carboxamide that are highly efficient and reproducible.

FIGURES

SUMMARY OF THE INVENTION

Figure 1:
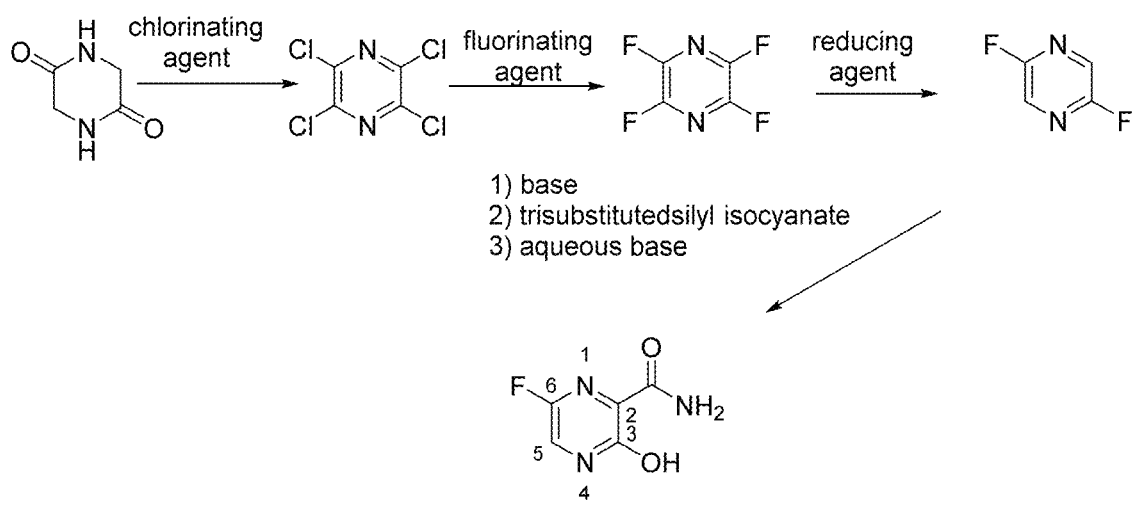
FIG. 1 is a chemical scheme for a method to prepare 6-fluoro-3-hydroxypyrazine-2-carboxamide.

In one aspect, disclosed herein is a method for preparing 6-fluoro-3-hydroxypyrazine-2-carboxamide. The method comprises: (a) contacting 2,5-diketopiperazine with a chlorinating agent or a mixture of two or more chlorinating agents to form 2,3,5,6-tetrachloroppyrazine; (b) contacting 2,3,5,6-tetrachloropyrazine with fluorinating agent in the presence of a solvent to form 2,3,5,6-tetrafluoropyrazine; (c) contacting 2,3,5,6-tetrafluoropyrazine with a reducing agent to form 2,5-difluoropyrazine; and (d) contacting 2,5-difluoropyrazine with a chlorinating agent or a mixture of two or more chlorinating agents to form 6-fluoro-3-hydroxypyrazine-2-carboxamide.

In another aspect, disclosed herein is a method for preparing 6-fluoro-3-hydroxypyrazine-2-carboxamide. The method comprises: (a) contacting 2,5-diketopiperazine with a chlorinating agent or a mixture of two or more chlorinating agents to form 2,3,5,6-tetrachloropyrazine; (b) contacting 2,3,5,6-tetrachloropyrazine with a fluorinating agent in the presence of a solvent to form 2,3,5,6-tetrafluoropyrazine; (c) contacting 2,3,5,6-tetrafluoropyrazine with an iridium catalyst, an organic base, and blue LEDS to form 2,5-difluoropiperazine; and (d) contacting 2,5-difluoropyrazine with a chlorinating agent or a mixture of two or more chlorinating agents to form 6-fluoro-3-hydroxypyrazine-2-carboxamide.

In yet another aspect, disclosed herein is a method for preparing 6-fluoro-3-hydroxypyrazine-2-carboxamide. The method comprises: (a) contacting 2,5-diketopiperazine with a chlorinating agent or the mixture of two or more chlorinating agents to form 2,3,5,6-tetrachloropyrazine; (b) contacting 2,3,5,6-tetrachloropyrazine with a fluorinating agent to form 2,3,5,6-tetrafluoropyrazine; (c) contacting 2,3,5,6-tetrafluoropyrazine with a Hantzch Ester in the presence of 405 nm light to form 2,5-difluoropyrazine; and (d) contacting 2,5-difluoropyrazine with a base and a trisubstitutedsilyl isocyanate to form 6-fluoro-3-hydroxypyrazine-2-carboxamide.

In still another aspect, disclosed herein is a method for preparing 6-fluoro-3-hydroxypyrazine-2-carboxamide. The method comprises: (a) contacting 2,5-difluoropyrazine with an organic base and an organic carbonate to form 3,6-difluoro-2-pyrazinecarboxylic acid alkyl ester; (b) contacting 3,6-difluoro-2-pyrazinecarboxylic acid alkyl ester with ammonium hydroxide to form 3,6-difluoro-2-pyrazinecarboxamide; and (d) contacting 3,6-difluoro-2-pyrazinecarboxamide with aqueous sodium bicarbonate to form 6-fluoro-3-hydroxypyrazine-2-carboxamide.

In an additional another aspect, disclosed herein is a method for preparing 6-fluoro-3-hydroxypyrazine-2-carboxamide. The method comprises: (a) contacting 2,5-difluoropyrazine with an organic base and carbon dioxide to form 3,6-difluoro-2-pyrazinecarboxylic acid; (b) contacting 3,6-difluoro-2-pyrazinecarboxylic acid with acylating agent followed by an alcohol and ammonium hydroxide to form 3,6-difluoro-2-pyrazinecarboxamide; and (c) contacting 3,6-difluoro-2-pyrazinecarboxamide with an aqueous base to form 6-fluoro-3-hydroxypyrazine-2-carboxamide.

In still another aspect, disclosed herein is a method for preparing 6-fluoro-3-hydroxypyrazine-2-carboxamide. The method comprises: (a) contacting 2,5-difluoropyrazine with a palladium (0) catalyst in the presence of cyanogen bromide and an inorganic base to form 3,6-difluoro-2-pyrazinecarbonitrile; (b) contacting 3,6-difluoro-2-pyrazinecarbonitrile with an aqueous acid to form 3,6-difluoro-2-pyrazinecarboxamide; and (c) contacting 3,6-difluoro-2-pyrazinecarboxamide with an aqueous base to form 6-fluoro-3-hydroxypyrazine-2-carboxamide.

In another aspect, disclosed herein is a method for preparing 6-fluoro-3-hydroxypyrazine-2-carboxamide. The method comprises: (a) contacting 2,3,5,6-tetrafluoropyrazine with an iridium catalyst, an organic base, and blue LEDs, a reducing agent, or a Hantzch ester to form 2,3,5-trifluoropyrazine; (b) contacting 2,3,5-trifluoropyrazine with an inorganic cyanide to form 3,6-difluoro-2-pyrazinecarbonitrile; (c) contacting 3,6-difluoro-2-pyrazinecarbonitrile with an aqueous acid to form 3,6-difluoro-2-pyrazinecarboxamide; and (d) contacting 3,6-difluoro-2-pyrazinecarboxamide with an aqueous base to form 6-fluoro-3-hydroxypyrazine-2-carboxamide.

In yet another aspect, disclosed herein is a method for preparing 6-fluoro-3-hydroxypyrazine-2-carboxamide. The method comprises: (a) contacting 2,3,5-trifluoropyrazine with ammonium hydroxide to form 3,6-difluoro-2-pyrazinamine; (b) contacting 3,6-difluoro-2-pyrazinamine with hydrogen cyanide and sodium nitrite to 3,6-difluoro-2-pyrazinecarbonitrile; (c) contacting 3,6-difluoro-2-pyrazinecarbonitrile with an aqueous acid to form 3,6-difluoro-2-pyrazinecarboxamide; and (d) contacting 3,6-difluoro-2-pyrazinecarboxamide with aqueous base to form 6-fluoro-3-hydroxypyrazine-2-carboxamide.

In still another aspect, disclosed herein is a method for preparing 6-fluoro-3-hydroxypyrazine-2-carboxamide. The method comprises: (a) contacting 2-aminopropanediamide with glyoxal to form 3-hydroxy-2-pyrazinecarboxamide; (b) contacting 3-hydroxy-2-pyrazinecarboxamide with 10% $F_2/N_2$ in the presence of an organic acid in a flow reactor to form 6-fluoro-3-hydroxypyrazine-2-carboxamide.

In another aspect, disclosed herein, is a method for preparing 6-fluoro-3-hydroxypyrazine-2-carboxamide. The method comprises: (a) contacting 3-hydroxy-2-pyrazinecarboxamide with an oxidant and maleic anhydride followed by a chlorinating agent to form 6-chloro-3,4-dihydro-3-oxo-2-pyrazinecarboxamide; and (b) contacting 6-chloro-3,4-dihydro-3-oxo-2-pyrazinecarboxamide with a fluorinating agent to form 6-fluoro-3-hydroxypyrazine-2-carboxamide.

The methods described above are highly efficient and shorter than current processes known in the art to prepare 6-fluoro-3-hydroxypyrazine-2-carboxamide. Other features and iterations of the invention are described in more detail below.

DETAILED DESCRIPTION OF THE INVENTION

The present disclosure provides methods for preparing favipiravir (6-fluoro-3-hydroxypyrazine-2-carboxamide). Favipiravir is a molecule that has shown sufficient anti-viral properties. These methods, as disclosed herein, utilize low cost starting materials and are shorter than other published processes.

(I) Methods Depicted in FIG. 1

One aspect of the present disclosure encompasses methods for the preparation of 6-fluoro-3-hydroxypyrazine-2-carboxamide. The method comprises: (a) contacting 2,5-diketopiperazine with a chlorinating agent or a mixture of two or more chlorinating agents to form 2,3,5,6-tetrachloropyrazine (b) contacting 2,3,5,6-tetrachloropyrazine with a fluorinating agent comprising a fluorinating agent in the presence of a solvent to form 2,3,5,6-tetrafluoropyrazine; (c) contacting 2,3,5,6-tetrafluoropyrazine with a reducing agent in the presence of a solvent to form 2,5-difluoropyrazine; and (d) contacting 2,5-difluoropyrazine with an organic base and an isocyanate followed by hydrolysis to form 6-fluoro-3-hydroxypyrazine-2-carboxamide according to the reaction scheme depicted in FIG. 1.

(a) Step (a)

As discussed above, Step (a) of the four step method involves contacting 2,5-diketopiperazine with a chlorinating agent or a mixture of two or more chlorinating agents. Non-limiting examples of suitable chlorinating agents may be phosphorus oxychloride, phosphorus pentachloride, phosphorus trichloride, oxalyl chloride, thionyl chloride, trichloroisocyanuric acid, and chlorine gas. In one embodiment, the chlorinating agent or the mixture of two or more chlorinating agents comprises phosphorus oxychloride, phosphorus pentachloride, and chlorine gas.

Generally, the mole ratio of 2,5-diketopiperazine to chlorinating agent or a mixture of two or more chlorinating agents may range from about 1.0:0.1 to about 1.0:100.0. In various embodiments, the mole ratio of 2,5-diketopiperazine to chlorinating agent or a mixture of two or more chlorinating agents may range from about 1.0:0.1 to about 1.0:100.0, from about 1.0:0.5 to about 1.0:50.0, or from about 1.0:1.0 to about 1.0:2.0.

Step (a), as detailed herein, may comprise a solvent. As recognized by those of skill in the art, the solvent can and will vary depending on the starting substrates, the catalyst, the ligand, the base, and the aromatic halide used in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (TH F), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In an embodiment, the reaction of Step (a) is conducted neat.

In general, the volume of the solvent to the weight ratio of 2,5-diketopiperazine will range from about 0.0:1 to about 500:1. In various embodiments, the volume of the solvent to weight ratio of 2,5-diketopiperazine may range from about 0.0:1 to about 500:1, from about 1:1 to about 250:1, from about 5:1 to about 200:1, or from about 10:1 to about 100:1. In an embodiment, the volume of the solvent to the weight ratio of 2,5-diketopiperazine may range from about 20:1 to about 75:1. In another embodiment, the volume of the solvent to the weight ratio of 2,5-diketopiperazine may ne 0.0:1.0.

In general, the reaction of Step (a) will be conducted at a temperature that ranges from about 25° C. to about 150° C. depending on the solvent utilized. In various embodiments, the temperature of the reaction may range from about 25° C. to about 150° C., from about 50° C. to about 140° C., or from about 80° C. to about 1300° C. The reaction typically is performed under ambient pressure to about 2 atmospheres. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,5-diketopiperazine. Typically, the amount 2,5-diketopiperazine remaining in the reaction mixture at the end of the reaction may be less than about 10%, less than about 5%, or less than about 2%.

2,3,5,6-Tetrachloropyrazine may be purified using a number of methods as known in the art. Non-limiting examples of these methods may be distillation, crystallization, or chromatography.

2,3,5,6-Tetrachloropyrazine may have a yield of at least about 60%. In various embodiments, 2,3,5,6-tetrachloropyrazine may have a yield of at least about 60%, at least about 65%, at least about 70%, at least about 75%, at least about 80%, at least about 85%, at least about 90%, at least about 95%, or at least about 99%.

(b) Step (b)

As discussed above, Step (b) of the four step method involves contacting 2,3,5,6-tetrachloropyrazine with a fluorinating agent to form 2,3,5,6-tetrafluoropyrazine. In an embodiment, Step (b) of the four step method utilizes a fluorinating agent and a phase transfer catalyst in the presence of a solvent.

A wide variety of fluorinating agents may be used in Step (b). Non-limiting examples of useful fluorinating agents may be LiF, NaF, KF, CsF, tetraethylammonium fluoride, and tetrabutylammonium fluoride. In an embodiment, the fluorinating agent comprises KF.

This step may optionally include a phase transfer catalyst (PTC). A wide variety of phase transfer catalysts may be used in Step (b) of the four step method. These phase transfer catalysts utilize various tetraalkylammonium salts. The anion of these salts may be chloride, bromide, iodide, carboxylate, or tosylate. Other non-limiting examples of phase transfer catalysts may be tetraethylammonium chloride, tetraethylammonium bromide, tetrabutylammonium chloride, tetrabutylammonium tosylate, benzyltributylammonium bromide, benzyldimethyloctylammonium chloride, benzyldimethyldecylammonium chloride, benzyltributylammonium chloride, and benzyltributylammonium bromide. In an embodiment, the phase transfer catalyst may be tetrabutylammonium bromide.

In general, the mole ratio of 2,3,5,6-tetrachloropyrazine to the fluorinating agent may range from about 1.0:4.0 to about 1.0:20.0. In various embodiments, the mole ratio of 2,3,5,6-tetrachloropyrazine to the fluorinating agent may range from about 1.0:4.0 to about 1.0:20.0, from about 1.0:6.0 to about 1.0:15.0, or from about 1.0:8.0 to about 1.0:12.0. In one embodiment, the mole ratio of 2,3,5,6-tetrachloropyrazine to fluorinating agent may be about 1.0:6.0.

Generally, the mole ratio of 2,3,5,6-tetrachloropyrazine to PTC may range from about 1.0:0.1 to about 1.0:10.0. In various embodiments, the mole ratio of 2,5-diketopiperazine to PTC may range from about 1.0:0.1 to about 1.0:10.0, from about 1.0:0.5 to about 1.0:5.0, or from about 1.0:1.0 to about 1.0:2.0. In one embodiment, the mole ratio of 2,3,5,6-tetrachloropyrazine to the PTC may be about 1.0:1.2.

Step (b), as detailed herein, may comprise a solvent. Suitable solvents are described in Section (I)(a). In one embodiment, the solvent is a polar aprotic solvent such as dimethylsulfoxide (DMSO).

In general, the volume to weight ratio of the solvent to 2,3,5,6-tetrachloropyrazine will range from about 0.5:1 to about 500:1. In various embodiments, the volume to weight ratio of the solvent to 2,3,5,6-tetrachloropyrazine may range from about 0.5:1 to about 500:1, from about 2:1 to about 250:1, from about 5:1 to about 200:1, or from about 10:1 to about 100:1. In an embodiment, the volume to weight ratio of the solvent to 2,3,5,6-tetrachloropyrazine may range from about 20:1 to about 75:1.

In general, the reaction of Step (b) will be conducted at a temperature that ranges from about 0° C. to about 100° C. depending on the solvent utilized. In various embodiments, the temperature of the reaction may range from about 0° C. to about 100° C., from about 25° C. to about 80° C., or from about 30° C. to about 70° C. In an embodiment, the temperature of the reaction may range from about 60° C. to about 70° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,3,5,6-tetrafluoropyrazine. Typically, the amount 2,3,5,6-tetrafluoropyrazine remaining in the reaction mixture at the end of the reaction may be less than about 10%, less than about 5%, or less than about 2%.

Suitable methods for purifying 2,3,5,6-tetrafluoropyrazine are known in the arts.

2,3,5,6-Tetrafluoropyrazine may have a yield of at least about 60%. In various embodiments, 2,3,5,6-tetrafluoropyrazine may have a yield of at least about 60%, at least about 65%, at least about 70%, at least about 75%, at least about 80%, at least about 85%, at least about 90%, at least about 95%, or at least about 99%.

(c) Step (c)

As discussed above, Step (c) of the four step process involves contacting 2,3,5,6-tetrafluoropyrazine with a reducing agent in the presence of a solvent to form 2,5-difluoropyrazine.

A variety of reducing agents may be used in Step (c) of the four step process. Non-limiting examples of reducing agents which may be utilized are LiBH$_4$, NaBH$_4$, NaCNBH$_3$, NaBH(OAc)$_3$, KBH$_4$, LiBHEt$_2$, or, LiBH$_x$R$_{(3-x)}$ where the R group is a carbon based substituent. In an embodiment, the reducing agent is NaBH$_4$.

Step (c), as detailed herein, may comprise a solvent. Suitable solvents are described in Section (I)(a). In an embodiment, the solvent is a polar aprotic solvent namely dimethylsulfoxide (DMSO).

In general, the mole ratio of 2,3,5,6-tetrafluoropyrazine to the reducing agent may range from about 1.0:0.25 to about 1.0:1.0. In various embodiments, the mole ratio of 2,3,5,6-tetrafluoropyrazine to the reducing agent may range from about 1.0:0.25 to about 1.0:1.0, from about 1.0:0.3 to about 1.0:0.8, or from about 1.0:0.5 to about 1.0:0.6. In one embodiment, the mole ratio of 2,3,5,6-tetrafluoropyrazine to the reducing agent may be about 1.0:0.55.

In general, the concentration of 2,3,5,6-tetrafluoropyrazine in the solvent may range from about 0.1M to about 5.0M. In various embodiments, the concentration of 2,3,5,6-tetrafluoropyrazine in the solvent may range from about 0.1M to about 5.0M, from about 0.5M to about 3.0M, from about 0.75 to about 1.25M. In one embodiment, the concentration of 2,3,5,6-tetrafluoropyrazine in the solvent may be about 1.0M.

In general, the reaction of Step (c) will be conducted at a temperature that ranges from about 0° C. to about 100° C. depending on the solvent utilized. In various embodiments, the temperature of the reaction may range from about 0° C. to about 100° C., from about 25° C. to about 80° C., or from about 30° C. to about 60° C. In one embodiment, the reaction of Step (c) may be about room temperature. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 minutes to about 1 hour. In this context, a "completed reaction" generally means that the reaction mixture contains a significantly diminished amount of 2,3,5,6-tetrafluoropyrazine. Typically, the amount 2,3,5,6-tetrafluoropyrazine remaining in the reaction mixture at the end of the reaction may be less than about 10%, less than about 5%, or less than about 2%.

Suitable methods for purifying 2,5-difluoropyrazine are described in the arts.

2,5-Difluoropyrazine may have a yield of at least about 60%. In various embodiments, 2,5-difluoropyrazine may have a yield of at least about 60%, at least about 65%, at least about 70%, at least about 75%, at least about 80%, at least about 85%, at least about 90%, at least about 95%, or at least about 99%.

(d) Step (d)

As discussed above, Step (d) of the four step method involves contacting 2,5-difluoropyrazine with an organic base to generate a carbanion. The carbanion is contacted with trisubstitutedsilyl isocyanate followed by an aqueous base to form 6-fluoro-3-hydroxypyrazine-2-carboxamide.

A variety of organic bases may be used in Step (d) of the four step method. Non-limiting examples of these other organic bases may be LiNH$_2$, lithium diisopropylamide, lithium bis(trimetylsilyl)amide, or lithium tetrametylpiperidine. In an embodiment, the organic base may be lithium diisopropylamide.

A variety of trisubstitutedsilyl isocyanate may be used in Step (d) of the four step method. Non-limiting examples of the trisubstitutedsilyl isocyanate may be trisubstitutedsilyl isocyanate where the substitution may be independently alkyl, alkylaryl, or aryl. In an embodiment, the trisubstitutedsilyl isocyanate may be trimethylsilyl isocyante.

In general, the mole ratio of 2,5-difluoropyrazine to organic base may range from about 1.0:1.0 to about 1.0:2.0. In various embodiments, the mole ratio of 2,5-difluoropyrazine to the organic base may range from about 1.0:1.0 to about 1.0:2.0, from about 1.0:1.0 to about 1.0:2.0, or from about 1.0:1.0 to about 1.0:1.5. In one embodiment, the mole ratio of 2,5-difluoropyrazine to the organic base may be about 1.0:1.1.

In general, the mole ratio of 2,5-difluoropyrazine to the trisubstitutedsilyl isocyanate may range from about 1.0:1.0 to about 1.0:2.0. In various embodiments, the mole ratio of 2,5-difluoropyrazine to the trisubstitutedsilyl isocyanate may range from about 1.0:1.0 to about 1.0:2.0, from about 1.0:1.0 to about 1.0:1.5.0, or from about 1.0:1.0 to about 1.0:1.2.

After a period of time after the trisubstitutedsilyl isocyanate is added, the reaction is contacted with an aqueous base to form 2,5-difluoropyrazine.

A wide variety of aqueous bases may be used. Non-limiting examples of suitable aqueous bases may be sodium bicarbonate, sodium carbonate, potassium bicarbonate, potassium carbonate, ammonium hydroxide, sodium hydroxide, potassium hydroxide, and lithium hydroxide. In an embodiment, the aqueous base may be aqueous sodium bicarbonate. The concentration of the aqueous base may range from about 0.01M to about 10.0M.

The mole ratio of 2,5-difluoropyrazine to the aqueous base may range from about 1.0:1.0 to about 1.0:20.0. In various embodiments, the mole ratio of 2,5-difluoropyrazine to the aqueous base may range from about 1.0:1.0 to about 1.0:20.0, from about 1.0:5.0 to about 1.0:15.0, or from about 1.0:8.0 to about 1.0:12.0.

In general, a reaction solvent is used in Step (d). A list of suitable solvents is described above in Section (I)(a). In one embodiment, the reaction solvent useful in Step (d) is tetrahydrofuran (THF). The quench solvent may be the same or different than the reaction solvent. In an embodiment, the quench solvent may be 1,4-dioxane.

Generally, the concentration of 2,5-difluoropyrazine in the solvent may range from about 0.5M to about 2.5M. In various embodiments, the concentration of 2,5-difluoropyrazine in the solvent may range from about 0.5M to about 2.5M, from about 0.75M to about 1.75M, from about 0.8M to about 1.25M.

In general, the reaction of Step (d) will be conducted at a temperature that ranges from about −25° C. to about 50° C. depending on the solvent utilized. In various embodiments, the temperature of the reaction may range from about −25° C. to about 50° C., from about −15° C. to about −30° C., or from about −10° C. to about 10° C. The reaction typically is performed under ambient pressure. The reaction may also be conducted under an inert atmosphere, for example under nitrogen, argon or helium.

Generally, the addition of sodium bicarbonate may occur at a different temperature. In various embodiments, the temperature of the addition of sodium bicarbonate may range from room temperature to about 100° C., from about 30° C. to about 80° C., or from 50° C. to about 70° C.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,5-difluoropyrazine. Typically, the amount 2,5-difluoropyrazine remaining in the reaction mixture at the end of the reaction may be less than about 10%, less than about 5%, or less than about 2%.

Suitable methods for purifying 2,5-difluoropyrazine are described in the arts.

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiments

Figure 2:
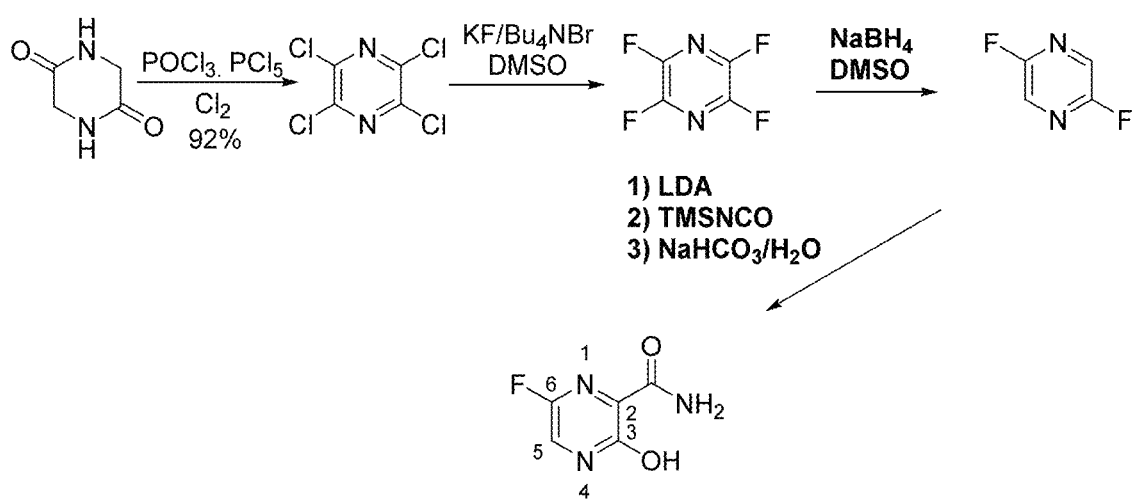
FIG. 2 is a chemical scheme for a preferred embodiment to prepare 6-fluoro-3-hydroxypyrazine-2-carboxamide according to FIG. 1.

In a preferred embodiment as shown in FIG. 2, the 2,5-diketopiperazine is contacted with phosphorus oxychloride, phosphorus pentachloride, and chlorine gas neat to form 2,3,5,6-tetrachloroppyrazine; the 2,3,5,6-tetrachloropyrazine is contacted with potassium fluoride and tetrabutylammonium fluoride in DMSO to form 2,3,5,6-tetrafluoropyrazine; contacting 2,3,5,6-tetrafluoropyrazine with NaBH$_4$ in DMSO to form 2,5-difluoropyrazine; contacting 2,5-difluoropyrazine with lithium diisopropylamide and trimethylsilyl isocyanate in THF to form 6-fluoro-3-hydroxypyrazine-2-carboxamide in at least a 60% yield.

Figure 3:
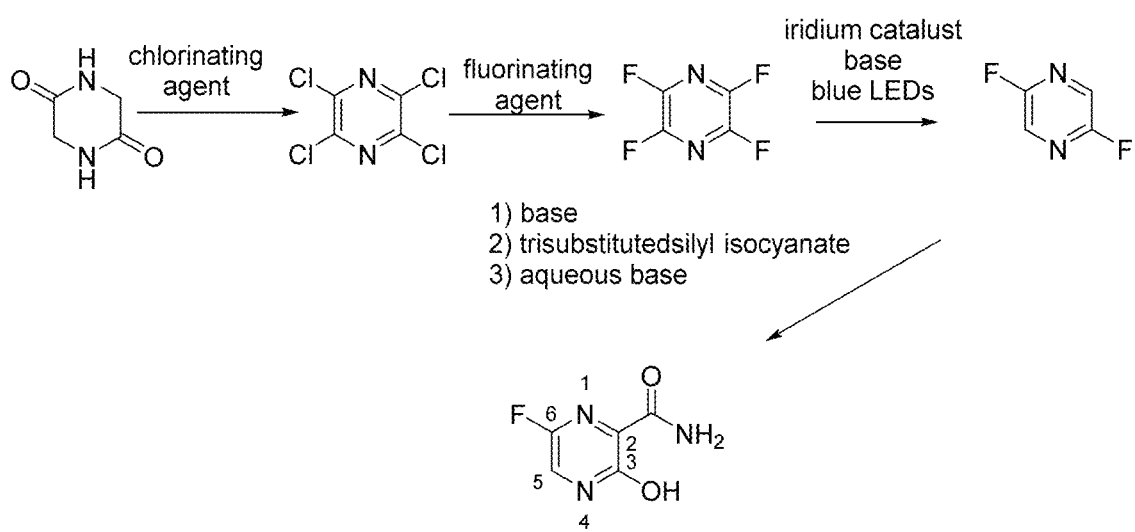
FIG. 3 is a chemical scheme for a method to prepare 6-fluoro-3-hydroxypyrazine-2-carboxamide.

(II) Method Depicted in FIG. 3

One aspect of the present disclosure encompasses methods for the preparation of 6-fluoro-3-hydroxypyrazine-2-carboxamide. The method comprises: (a) contacting 2,5-diketopiperazine with a chlorinating agent or a mixture of two or more chlorinating agents to form 2,3,5,6-tetrachloroppyrazine (b) contacting 2,3,5,6-tetrachloropyrazine with a fluorinating agent to form 2,3,5,6-tetrafluoropyrazine; (c) contacting 2,3,5,6-tetrafluoropyrazine with an iridium catalyst, an organic bae, and blue LEDs to form 2,5-difluoropiperazine; and (d) contacting 2,5-difluoropyrazine with an organic base to generate a carbanion. The carbanion is contacted with trisubstitutedsilyl isocyanate followed by an aqueous base to form 6-fluoro-3-hydroxypyrazine-2-carboxamide as shown in FIG. 3.

(a) Step (a)

Step (a) of the four step process is described in more detail above in section (I)(a).

(b) Step (b)

Step (b) of the four step process is described in more detail above in section (I)(b).

(c) Step (c)

Step (c) of the four step process encompasses contacting the 2,3,5,6-tetrafluoropyrazine with an iridium catalyst, an organic base, and blue LEDs.

A wide variety of iridium catalysts may be used in Step (c) of the four step method. Non-limiting examples of these catalysts may be Ir(Fppy)$_3$, Ir(ppy)$_3$, Ir(dFppy)$_3$, Ir(F-(t-Bu)-ppy))$_3$, Ir(dF-(t-Bu)-ppy)$_3$, phenoxazine iridium photocatalysts, and phenothiazine iridium photocatalysts. In an embodiment, the iridium catalyst may be Ir(ppy)$_3$.

Numerous organic bases may be used in Step (c) of the four step method. Non-limiting examples of useful bases may be trimethylamine, diispropylethylamine (DIPEA), triethylamine, dimethylbenzylamine, tributylamine, or triphenylamine. In an embodiment, the useful base used in Step (c) of the four step method may be diisopropylethylamine (DIPEA).

Generally, the mole ratio of 2,3,5,6-tetrafluoropyrazine to the iridium catalyst may range from about 1.0:0.01 to about 1.0:0.5. In various embodiments, the mole ratio of 2,3,5,6-tetrafluoropyrazine to the iridium catalyst may range from about 1.0:0.01 to about 1.0:0.5, from about 1.0:0.05 to about 1.0:0.1, or from about 1.0:0.1 to about 1.0:0.3.

In general, the mole ratio of 2,3,5,6-tetrafluoropyrazine to the base may range from about 1.0:1.0 to about 1.0:10.0. In various embodiments, the mole ratio of 2,3,5,6-tetrafluoropyrazine to the base may range from about 1.0:1.0 to about 1.0:10.0, from about 1.0:2.0 to about 1.0:8.0, or from about 1.0:4.0 to about 1.0:6.0.

Step (c) of the four step process is conducted in the presence of a solvent. Suitable solvents are described above in Section (I)(a). In one embodiment, the solvent useful in the Step (c) is acetonitrile.

In general, the concentration of 2,3,5,6-tetrafluoropyrazine in the solvent may range from about 0.1M to about 1.0M. In various embodiments, the concentration of 2,3,5,6-tetrafluoropyrazine in the solvent may range 0.1M to about 1.0M, from about 0.1M to about 0.75M1, or from about 0.2M to about 0.5M.

In general, the reaction of Step (c) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 35° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,3,5,6-tetrafluoropyrazine. Typically, the amount 2,3,5,6-tetrafluoropyrazine remaining in the reaction mixture at the end of the reaction may be less than about 10%, less than about 5%, or less than about 2%.

Suitable methods for purifying 2,5-difluoropyrazine are described in the arts.

2,5-Difluoropyrazine may have a yield of at least about 60%. In various embodiments, 2,5-difluoropyrazine may have a yield of at least about 60%, at least about 65%, at least about 70%, at least about 75%, at least about 80%, at least about 85%, at least about 90%, at least about 95%, or at least about 99%.

(d) Step (d)

Step (d) of the four step process is described in more detail above in section (I)(d).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiments

Figure 4:
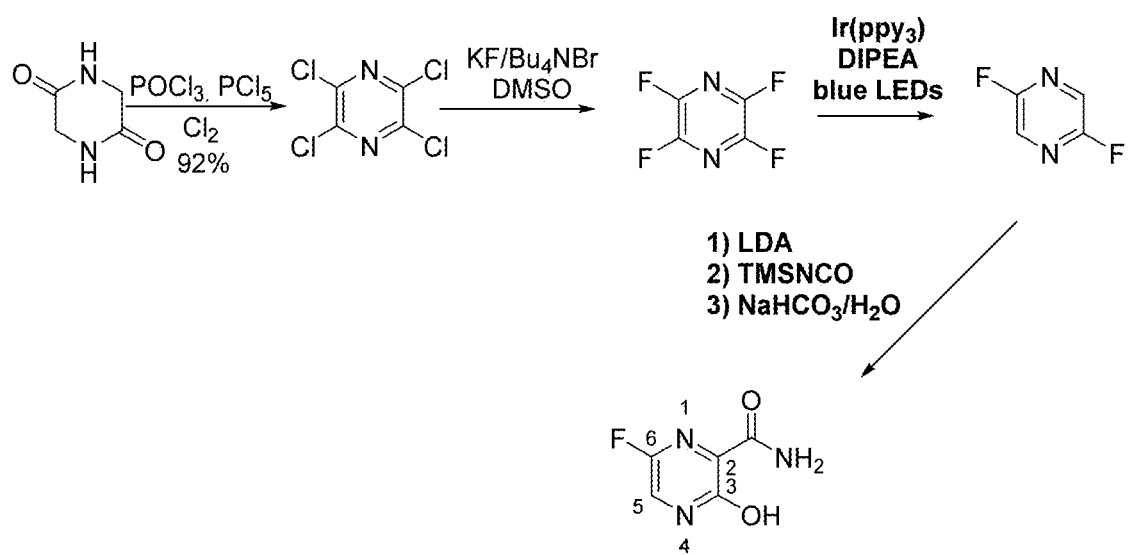
FIG. 4 is a chemical scheme for a preferred embodiment to prepare 6-fluoro-3-hydroxypyrazine-2-carboxamide according to FIG. 3.

In a preferred embodiment as shown in FIG. 4, the 2,5-diketopiperazine is contacted with phosphorus oxychloride, phosphorus pentachloride, and chlorine gas to form 2,3,5,6-tetrachloropyrazine; the 2,3,5,6-tetrachloropyrazine is contacted with potassium fluoride and tetrabutylammonium bromide to form 2,3,5,6-tetrafluoropyrazine; the 2,3,5,6-tetrafluoropyrazine is contacted with Ir(py)$_3$, diisopropylethylamine, and blue LEDs to form 2,5-difluoropyrazine; the 2,5-difluoropyrazine is contacted with lithium diisopropylamide and trimethylsilyl isocyanate to form 6-fluoro-3-hydroxypyrazine-2-carboxamide in at least a 60% yield.

Figure 5:
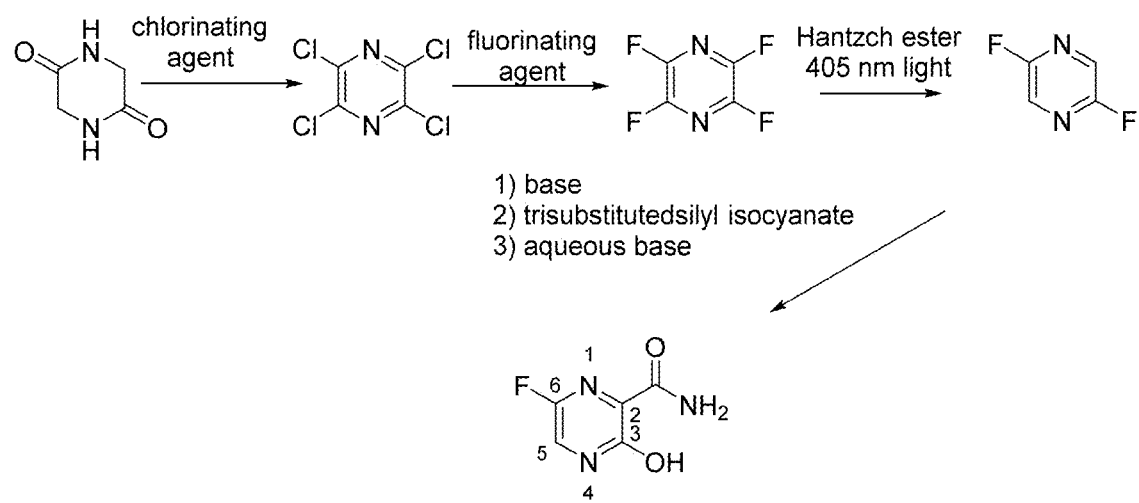
FIG. 5 is a chemical scheme for a method to prepare 6-fluoro-3-hydroxypyrazine-2-carboxamide.

(III) Method Depicted in FIG. 5

One aspect of the present disclosure encompasses methods for the preparation of 6-fluoro-3-hydroxypyrazine-2-carboxamide. The method comprises: (a) contacting 2,5-diketopiperazine with a chlorinating agent or a mixture of two or more chlorinating agents to form 2,3,5,6-tetrachloropyrazine (b) contacting 2,3,5,6-tetrachloropyrazine with a fluorinating agent to form 2,3,5,6-tetrafluoropyrazine; (c) contacting 2,3,5,6-tetrafluoropyrazine with a Hantzch ester in the presence of 405 nm light to form 2,5-difluoropyrazine; and (d) contacting 2,5-difluoropyrazine with an organic base to generate a carbanion. The carbanion is contacted with trisubstitutedsilyl isocyanate followed by an aqueous base to form 6-fluoro-3-hydroxypyrazine-2-carboxamide as shown in FIG. 5.

(a) Step (a)

Step (a) of the four step method is described in more detail above in section (I)(a).

(b) Step (b)

Step (b) of the four step method is described in more detail above in section (I)(b).

(c) Step (c)

Step (c) of the four step method encompasses contacting the 2,3,5,6-tetrafluoropyrazine with a Hantzch ester in the presence of 405 nm light to form 2,5-difluoropyrazine.

Generally, the Hantzch ester may be used and represented by the following formula shown below:

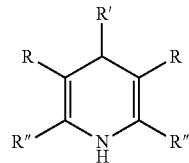

wherein R is selected from a group consisting of a nitrile, an alkyl ester, a substituted alkyl ester, an alkyl amide, a substituted alkyl amide, a carboxylic acid, an alkyl thioester, or an alkyl substituted thioester; R' is selected from deuterium, an alkyl group, or a substituted alkyl group; and R" is hydrogen, deuterium, an alkyl group or a substituted alkyl group. In an embodiment, the Hantzch ester may be diethyl 1,4-dihydro-2,6-dimethyl-3,5-pyridinedicarboxylate.

In general, the mole ratio of 2,3,5,6-tetrafluoropyrazine to Hantzch ester may range from about 1.0:1.0 to about 1.0:3.0. In various embodiments, the mole ratio of 2,3,5,6-tetrafluoropyrazine to Hantzch ester may range from about 1.0:1.0 to about 1.0:3.0, from about 1.0:1.0 to about 1.0:2.0, or from about 1.0:1.1 to about 1.0:1.5.

Step (c) of the four step method is conducted in the presence of a solvent. Suitable solvents are described above in Section (I)(a). In one embodiment, the solvent useful in the Step (c) is dimethylformamide (DMF).

In general, the concentration of 2,3,5,6-tetrafluoropyrazine in the solvent may range from about 0.1M to about 1.0M. In various embodiments, the concentration of 2,3,5,6-tetrafluoropyrazine in the solvent may range from about 0.1M to about 1.0M, from about 0.25M, from about 0.75M, or from about 0.4M to about 0.6M.

In general, the reaction of Step (c) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 40° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,3,5,6-tetrafluoropyrazine. Typically, the amount 2,3,5,6-tetrafluoropyrazine remaining in the reaction mixture at the end of the reaction may be less than about 10%, less than about 5%, or less than about 2%.

Suitable methods for purifying 2,5-difluoropyrazine are described in Section (I)(c).

2,5-Difluoropyrazine may have a yield of at least about 60%. In various embodiments, 2,5-difluoropyrazine may have a yield of at least about 60%, at least about 65%, at least about 70%, at least about 75%, at least about 80%, at least about 85%, at least about 90%, at least about 95%, or at least about 99%.

(d) Step (d)

Step (d) of the four step process is described in more detail above in section (I)(d).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiments

Figure 6:
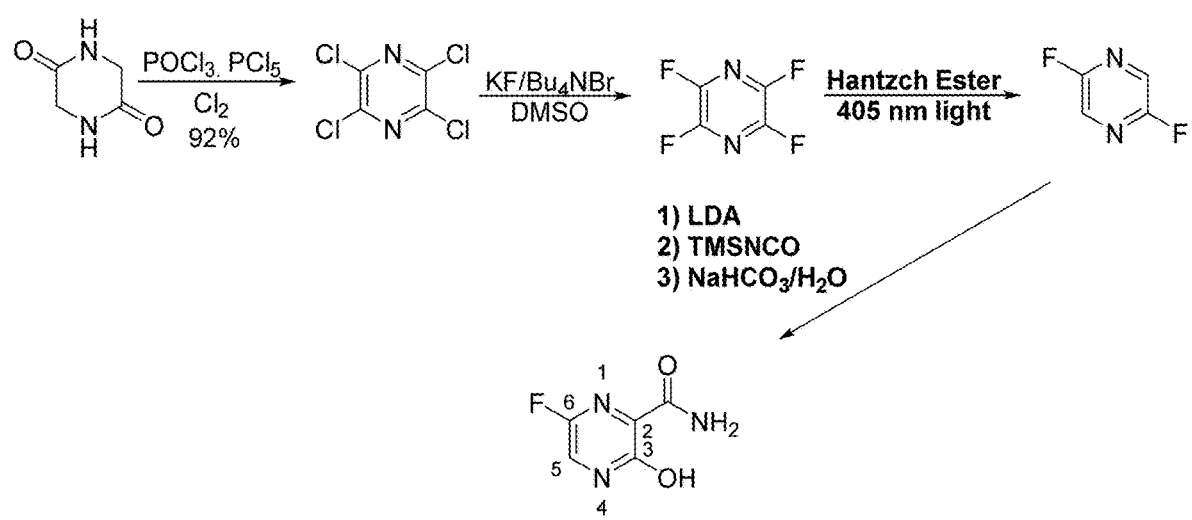
FIG. 6 is a chemical scheme for a preferred embodiment to prepare 6-fluoro-3-hydroxypyrazine-2-carboxamide according to FIG. 5.

In a preferred embodiment as shown in FIG. 6, the 2,5-diketopiperazine is contacted with phosphorus oxychloride, phosphorus pentachloride, and chlorine gas to form 2,3,5,6-tetrachloropyrazine; the 2,3,5,6-tetrachloropyrazine is contacted with potassium fluoride and tetrabutylammonium bromide to form 2,3,5,6-tetrafluoropyrazine; the 2,3,5,6-tetrafluoropyrazine is contacted with 1,4-dihydro-2,6-dimethyl-3,5-pyridinedicarboxylate in the presence of 405 nm light to form 2,5-difluoropyrazine; the 2,5-difluoropyrazine is contacted with lithium diisopropylamide and trimethylsilyl isocyanate to form 6-fluoro-3-hydroxypyrazine-2-carboxamide in at least a 60% yield.

Figure 7:
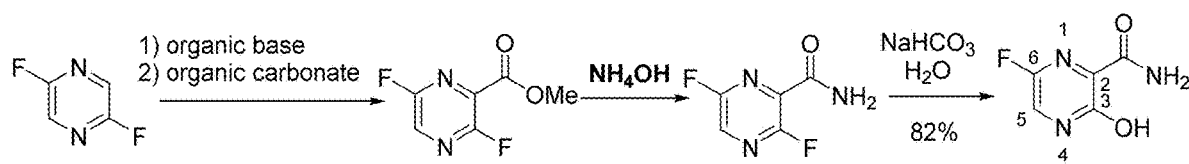
FIG. 7 is a chemical scheme for a method to prepare 6-fluoro-3-hydroxypyrazine-2-carboxamide.

(IV) Method Depicted in FIG. 7

One additional aspect of the present disclosure encompasses methods for the preparation of 6-fluoro-3-hydroxypyrazine-2-carboxamide. The method comprises: (a) contacting 2,5-difluoropyrazine with an organic base and an organic carbonate to form 3,6-difluoro-2-pyrazinecarboxylic acid alkyl ester; (b) contacting 3,6-difluoro-2-pyrazinecarboxylic acid alkyl ester with ammonium hydroxide to form 3,6-difluoro-2-pyrazinecarboxamide; and (c) contacting 3,6-difluoro-2-pyrazinecarboxamide with aqueous base to form 6-fluoro-3-hydroxypyrazine-2-carboxamide according to the reaction scheme depicted in FIG. 7. The preparation of 2,5-difluoropyrazine is described in more detail in Sections (I)(a) through (I)(c).

(a) Step (a)

Step (a) of the three step process encompasses contacting the 2,5-difluoropyrazine with base forming an anion. Quenching the anion with an organic carbonate forms 3,6-difluoro-2-pyrazinecarboxylic acid alkyl ester.

A variety of organic bases may be used in Step (a) of the three step method. Non-limiting examples of these bases may be LiNH$_2$, lithium diisopropylamide, lithium bis(trimetylsilyl)amide, or lithium tetrametylpiperidine. In an embodiment, the organic base may be lithium diisopropylamide.

Numerous organic carbonates may be used in Step (a) of the three step method. Non-limiting examples of the organic carbonates may be dimethyl carbonate, diethyl carbonate, or ethylene carbonate, or trimethylene carbonate. In an embodiment, the organic carbonate may be dimethyl carbonate.

In general, the mole ratio of 2,5-difluoropyrazine to the base may range from about 1.0:1.0 to about 1.0:1.5. In various embodiments, the mole ratio of 2,5-difluoropyrazine to the base may range from about 1.0:1.0 to about 1.0:1.5, from about 1.0:1.0 to about 1.0:1.3, or from about 1.0:1.0 to about 1.0:1.2.

In general, the mole ratio of 2,5-difluoropyrazine to organic carbonate may range from about 1.0:1.0 to about 1.0:2.0. In various embodiments, the mole ratio of 2,5-difluoropyrazine to organic carbonate may range from about 1.0:1.0 to about 1.0:2.0, from about 1.0:1.0 to about 1.0:1.5, or from about 1.0:1.0 to about 1.0:1.3.

After a period of time after organic carbonate is added, the reaction is contacted with water to quench the reaction.

In general, a solvent is used in Step (a). A list of suitable solvents is described above in Section (I)(a). The solvent useful in Step (d) is tetrahydrofuran (THF).

Generally, the concentration of 2,5-difluoropyrazine in the solvent may range from about 0.1M to about 2.0M. In various embodiments, the concentration of 2,5-difluoropyrazine in the solvent may range from about 0.1M to about 2.0M, from about 0.5M to about 1.5M, or from about 0.5M to about 1.25M.

In general, the reaction of Step (b) may be conducted at a temperature that ranges from about −50° C. to about 25° C. In various embodiments, the temperature of the reaction may range from about −50° C. to about 25° C., from about −25° C. to about −15° C., or from about −15° C. to about 10° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,5-difluoropyrazine. Typically, the amount 2,5-difluoropyrazine remaining in the reaction mixture at the end of the reaction may be less than about 10%, less than about 5%, or less than about 2%.

Suitable methods for purifying 3,6-difluoro-2-pyrazinecarboxylic acid methyl ester are described in Section (I)(a).

3,6-Difluoro-2-pyrazinecarboxylic acid methyl may have a yield of at least about 60%. In various embodiments, 3,6-difluoro-2-pyrazinecarboxylic acid methyl may have a yield of at least about 60%, at least about 65%, at least about 70%, at least about 75%, at least about 80%, at least about 85%, at least about 90%, at least about 95%, or at least about 99%.

(b) Step (b)

Step (b) of the four Step process encompasses contacting the 3,6-difluoro-2-pyrazinecarboxylic acid alkyl ester with ammonium hydroxide to form 3,6-difluoro-2-pyrazinecarboxamide.

In general, the mole ratio of 3,6-difluoro-2-pyrazinecarboxamide to ammonium hydroxide in the quench may range from about 1.0:2.0 to about 1.0:100.0. In various embodiments, the mole ratio of 3,6-difluoro-2-pyrazinecarboxamide to ammonium hydroxide in the quench may range from about 1.0:2.0 to about 1.0:100.0, from about 1.0:5.0 to about 1.0:80.0, or from about 1.0:10.0 to about 1.0:50.0.

Step (b) of the three step method may be conducted in the presence of a solvent. Suitable solvents are described above in Section (I)(a). In one embodiment, the solvent useful in the Step (b) is methanol.

In general, the concentration of 3,6-difluoro-2-pyrazinecarboxamide in the solvent may range from about 0.01M to about 1.0M. In various embodiments, the concentration of 3,6-difluoro-2-pyrazinecarboxamide in the solvent may range from about 0.01M to about 1.0M, from about 0.05M to about 0.5M, from about 0.08M to about 0.12M.

In general, the reaction of Step (b) will be conducted at a temperature that ranges from about 0° C. to about 100° C. depending on the solvent utilized. In various embodiments, the temperature of the reaction may range from about 0° C. to about 100° C., from about 25° C. to about 80° C., or from about 30° C. to about 60° C. In one embodiment, the reaction temperature of Step (b) may be about room temperature. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3,6-difluoro-2-pyrazinecarboxylic acid methyl ester. Typically, the amount 3,6-difluoro-2-pyrazinecarboxylic acid methyl ester remaining in the reaction mixture at the end of the reaction may be less than about 10%, less than about 5%, or less than about 2%.

Suitable methods for purifying 3,6-difluoro-2-pyrazinecarboxamide are described in Section (I)(a).

3,6-difluoro-2-pyrazinecarboxamide may have a yield of at least about 60%. In various embodiments, 3,6-difluoro-2-pyrazinecarboxamide may have a yield of at least about 60%, at least about 65%, at least about 70%, at least about 75%, at least about 80%, at least about 85%, at least about 90%, at least about 95%, or at least about 99%.

(d) Step (c)

Step (c) of the three step method encompasses contacting the 3,6-difluoro-2-pyrazinecarboxamide with an aqueous base to form 6-fluoro-3-hydroxypyrazine-2-carboxamide.

Numerous aqueous bases may be used in Step (c) of the three step method. Non-limiting examples of these bases may be sodium carbonate, potassium carbonate, lithium bicarbonate, sodium bicarbonate, potassium bicarbonate, cesium bicarbonate, calcium bicarbonate, magnesium bicarbonate, sodium hydroxide, lithium hydroxide, potassium hydroxide, or calcium hydroxide. In an embodiment, the aqueous base useful in Step (c) of the three step method is sodium bicarbonate.

An optional acid may be used with the aqueous base to reduce the pH to the appropriate value. Non-limiting examples of optional acids are hydrochloric acid, sulfuric acid, acetic acid, phosphoric acid, or citric acid.

The reaction is contacted with aqueous base to quench the reaction. The concentration of the aqueous base will range from about 0.1 M to about a saturated solution. Generally, an excess of aqueous base is normally used.

In general, a solvent is used in Step (c) of the method. A list of suitable solvents is described above in Section (I)(a). In one embodiment, the solvent useful in Step (c) is 1,4-dioxane.

Generally, the volume to weight ratio of the solvent to 3,6-difluoro-2-pyrazinecarboxamide will range from about 0.5:1 to about 500:1. In various embodiments, the volume to weight ratio of the solvent to 3,6-difluoro-2-pyrazinecarboxamide may range from about 0.5:1 to about 500:1, from about 2:1 to about 250:1, from about 5:1 to about 200:1, or from about 10:1 to about 100:1. In an embodiment, the volume to weight ratio of the solvent to 2,5-difluoropyrazine may range from about 20:1 to about 75:1.

In general, the reaction of Step (c) will be conducted at a temperature that ranges from about 0° C. to about 100° C. depending on the solvent utilized. In various embodiments, the temperature of the reaction may range from about 0° C. to about 100° C., from about 25° C. to about 75° C., or from about 40° C. to about 60° C. In one embodiment, the temperature of Step (c) may be about 60° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3,6-difluoro-2-pyrazinecarboxamide. Typically, the amount 3,6-difluoro-2-pyrazinecarboxamide remaining in the reaction mixture at the end of the reaction may be less than about 10%, less than about 5%, or less than about 2%.

Suitable method for purifying 6-fluoro-3-hydroxypyrazine-2-carboxamide are described in Section (I)(a).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 8:
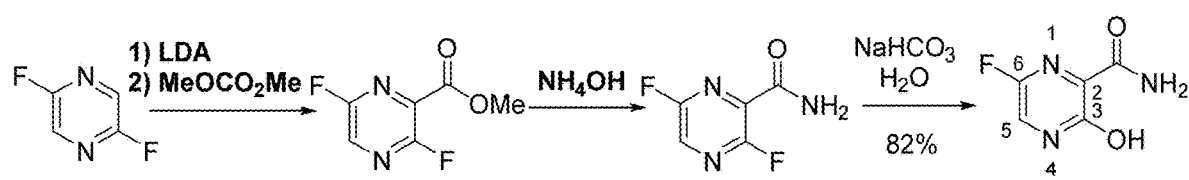
FIG. 8 is a chemical scheme for a preferred embodiment to prepare 6-fluoro-3-hydroxypyrazine-2-carboxamide according to FIG. 7.

In a preferred embodiment as shown in FIG. 8, the 2,5-diketopiperazine is contacted with lithium diisopropylamide and dimethylcarbonate to form 3,6-difluoro-2-pyrazinecarboxylic acid methyl ester; the 3,6-difluoro-2-pyrazinecarboxylic acid methyl ester is contacted with ammonium hydroxide to form 3,6-difluoro-2-pyrazinecarboxamide; and the 3,6-difluoro-2-pyrazinecarboxamide is contacted with aqueous sodium bicarbonate to form 6-fluoro-3-hydroxypyrazine-2-carboxamide in at least a 60% yield.

Figure 9:
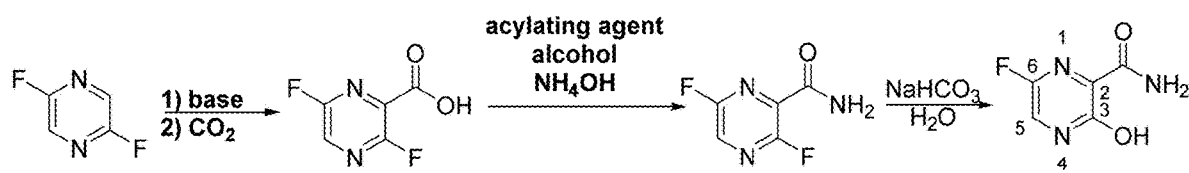
FIG. 9 is a chemical scheme for a method to prepare 6-fluoro-3-hydroxypyrazine-2-carboxamide.

(V) Method Depicted in FIG. 9

One additional aspect of the present disclosure encompasses methods for the preparation of 6-fluoro-3-hydroxypyrazine-2-carboxamide. The method comprises: (a) contacting 2,5-difluoropyrazine with an organic base and carbon dioxide to form 3,6-difluoro-2-pyrazinecarboxylic acid; (b) contacting 3,6-difluoro-2-pyrazinecarboxylic acid with an acylating agent followed by an alcohol and ammonium hydroxide to form 3,6-difluoro-2-pyrazinecarboxamide; and (c) contacting 3,6-difluoro-2-pyrazinecarboxamide with an aqueous base to form 6-fluoro-3-hydroxypyrazine-2-carboxamide. according to the reaction scheme depicted in FIG. 9. The preparation of 2,5-difluoropyrazine is described in more detail in Sections (I)(a) through (I)(c).

(a) Step (a)

Step (a) of the three step method encompasses contacting the 2,5-difluoropyrazine with organic base forming an anion. Quenching the anion with carbon dioxide forms 3.6-difluoro-2-pyrazinecarboxylic acid. Other organic bases are described in more detail above. In an embodiment, the organic base is lithium diisopropylamide.

In general, the mole ratio of 2,5-difluoropyrazine to the organic base may range from about 1.0:1.0 to about 1.0:2.0. In various embodiments, the mole ratio of 2,5-difluoropyrazine to the organic base may range from about 1.0:1.0 to about 1.0:2.0, from about 1.0:1.0 to about 1.0:1.5, or from about 1.0:1.0 to about 1.0:1.2.

In general, carbon dioxide is used in excess in this reaction step.

After a period of time after carbon dioxide is added, the reaction is contacted with water to quench the reaction and the pH is adjusted to approximately 1.0. Various acids may be used to adjust the pH. Non-limiting examples of acids are hydrochloric acid, sulfuric acid, or phosphoric acid.

In general, a solvent is used in Step (a). A list of suitable solvents is described above in Section (I)(a). In one embodiment, the solvent useful in Step (d) is tetrahydrofuran (THF).

Generally, the volume to weight ratio of the solvent to 2,5-difluoropyrazine will range from about 0.5:1 to about 500:1. In various embodiments, the volume to weight ratio of the solvent to 2,5-difluoropyrazine may range from about 0.5:1 to about 500:1, from about 2:1 to about 250:1, from about 5:1 to about 200:1, or from about 10:1 to about 100:1. In an embodiment, the volume to weight ratio of solvent to 2,5-difluoropyrazine may range from about 20:1 to about 75:1.

In general, the reaction of Step (a) will be conducted at a temperature that ranges from about −25° C. to about 25° C. depending on the solvent utilized. In various embodiments, the temperature of the reaction may range from about −25° C. to about 25° C., from about −10° C. to about 20° C., or from about −5° C. to about 10° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,5-difluoropyrazine. Typically, the amount 2,5-difluoropyrazine remaining in the reaction mixture at the end of the reaction may be less than about 10%, less than about 5%, or less than about 2%.

Suitable methods for purifying 3,6-difluoro-2-pyrazinecarboxylic acid are described in the arts.

3,6-Difluoro-2-pyrazinecarboxylic acid may have a yield of at least about 60%. In various embodiments, 3,6-difluoro-2-pyrazinecarboxylic acid may have a yield of at least about 60%, at least about 65%, at least about 70%, at least about 75%, at least about 80%, at least about 85%, at least about 90%, at least about 95%, or at least about 99%.

(b) Step (b)

Step (b) of the three step method encompasses contacting the 3,6-difluoro-2-pyrazinecarboxylic acid with acylating agent forming a carbonyl chloride. After the carbonyl chloride is formed, the reaction is initially quenched with an alcohol followed to form 3,6-difluoro-2-pyrazinecarboxamide.

Numerous acylating agents may be used in Step (b) of the three step method. Non-limiting examples of these acylating agents may be may be sulfuryl chloride, thionyl chloride, oxalyl chloride, phosphorus oxychloride, or phosgene. In an embodiment, the acylating agent is thionyl chloride.

A wide variety of alcohols may be used in Step (b) of the three step method. Non-limiting examples may be methanol, ethanol, benzyl alcohol, propanol, and butanol. In an embodiment, the alcohol useful in Step (b) is methanol.

In general, the mole ratio of 3,6-difluoro-2-pyrazinecarboxylic acid to acylating agent may range from about 1.0:1.0 to about 1.0:10.0. In various embodiments, the mole ratio of 3,6-difluoro-2-pyrazinecarboxamide to acylating agent may range from about 1.0:1.0 to about 1.0:10.0, from about 1.0:2.0 to about 1.0:8.0, or from about 1.0:3.0 to about 1.0:6.0.

In general, the mole ratio of alcohol to 3,6-difluoro-2-pyrazinecarboxylic acid used may range from about 1.0:1.0 to about 200.0:1.0. In various embodiments, the mole ratio of methanol to 3,6-difluoro-2-pyrazinecarboxylic acid used may range from about 1.0:1.0 to about 200.0:1.0, from about 7.0:1.0 to about 100.0:1.0, or from about 9.0:1.0 to about 20.0:1.0.

Step (b) of the three Step method may be conducted in the presence of a solvent. Suitable solvents are described above in Section (I)(a). In one embodiment, the solvent useful in the Step (b) is dichloromethane (DCM).

In general, the volume to weight ratio of solvent to 3,6-difluoro-2-pyrazinecarboxylic acid will range from about 0.5:1 to about 500:1. In various embodiments, the volume to weight ratio of the solvent to 3,6-difluoro-2-pyrazinecarboxylic acid may range from about 0.5:1 to about 500:1, from about 2:1 to about 250:1, from about 5:1 to about 200:1, or from about 10:1 to about 100:1. In an embodiment, the volume to weight ratio of solvent to 3,6-difluoro-2-pyrazinecarboxylic acid may range from about 20:1 to about 75:1.

In general, the reaction of Step (b) will be conducted at a temperature that ranges from about 0° C. to about 100° C. depending on the solvent utilized. In various embodiments, the temperature of the reaction may range from about 0° C. to about 100° C., from about 25° C. to about 80° C., or from about 30° C. to about 60° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 30 minutes. In this context, a "completed reaction" generally means that the reaction mixture contains a significantly diminished amount of 3,6-difluoro-2-pyrazinecarboxylic acid. Typically, the amount 3,6-difluoro-2-pyrazinecarboxylic acid remaining in the reaction mixture at the end of the reaction may be less than about 10%, less than about 5%, or less than about 2%.

In general, the quenching of the carbonyl chloride in the reaction of Step (b) with an alcohol will be conducted at a temperature that ranges from about −10° C. to about 25° C. depending on the solvent utilized. In various embodiments, the temperature of the reaction may range from about −10° C. to about 25° C., from about −5° C. to about 20° C., or from about −50° C. to about 10° C. The reaction typically is performed under ambient pressure. The reaction may also be conducted under an inert atmosphere, for example under nitrogen, argon or helium. After the quench is complete, the reaction Step (b) is warmed to room temperature.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3,6-difluoro-2-pyrazinecarbonyl chloride. Typically, the amount 3,6-difluoro-2-pyrazinecarbonyl chloride remaining in the reaction mixture at the end of the reaction may be less than about 10%, less than about 5%, or less than about 2%.

After the ester is formed, the reaction is stirred with ammonium hydroxide to form the 3,6-difluoro-2-pyrazinecarboxamide. Suitable condition are found above in Section (IV)(b).

Suitable methods for purifying 3,6-difluoro-2-pyrazinecarboxamide are described in Section (I)(a).

3,6-difluoro-2-pyrazinecarboxamide may have a yield of at least about 60%. In various embodiments, 3,6-difluoro-2-pyrazinecarboxamide may have a yield of at least about 60%, at least about 65%, at least about 70%, at least about 75%, at least about 80%, at least about 85%, at least about 90%, at least about 95%, or at least about 99%.

(d) Step (c)

Step (c) of the three step process encompasses contacting the 3,6-difluoro-2-pyrazinecarboxamide with an aqueous base to form 6-fluoro-3-hydroxypyrazine-2-carboxamide. Suitable amounts of material and conditions are described above in Section (IV)(c).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 10:
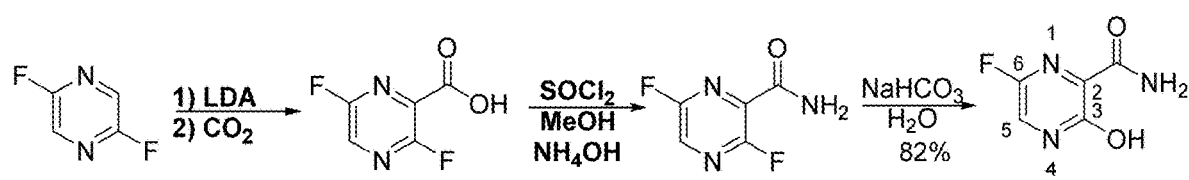
FIG. 10 is a chemical scheme for a preferred embodiment to prepare 6-fluoro-3-hydroxypyrazine-2-carboxamide according to FIG. 9.

In a preferred embodiment as shown in FIG. 10, the 2,5-diketopiperazine is contacted with lithium diisopropylamide and carbon dioxide to form 3,6-difluoro-2-pyrazinecarboxylic acid; the 3,6-difluoro-2-pyrazinecarboxylic acid is contacted with thionyl chloride and methanol and ammonium hydroxide to form 3,6-difluoro-2-pyrazinecarboxamide; and the 3,6-difluoro-2-pyrazinecarboxamide is contacted with aqueous sodium bicarbonate to form 6-fluoro-3-hydroxypyrazine-2-carboxamide in at least a 60% yield.

Figure 11:
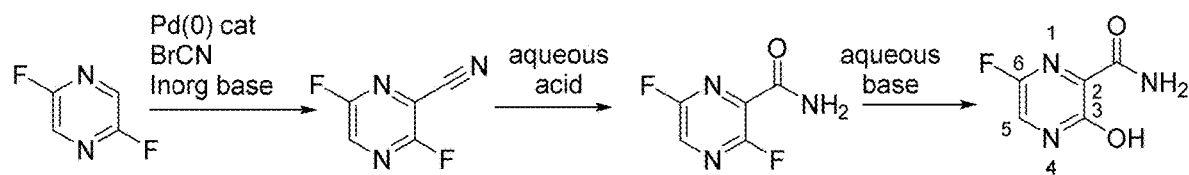
FIG. 11 is a chemical scheme for a method to prepare 6-fluoro-3-hydroxypyrazine-2-carboxamide.

(VI) Method Depicted in FIG. 11

One additional aspect of the present disclosure encompasses methods for the preparation of 6-fluoro-3-hydroxypyrazine-2-carboxamide. The method comprises: (a) contacting 2,5-difluoropyrazine with a palladium (0) catalyst in the presence of cyanogen bromide and an inorganic base to form 3,6-difluoro-2-pyrazinecarbonitrile; (b) contacting 3,6-difluoro-2-pyrazinecarbonitrile with an aqueous acid to form 3,6-difluoro-2-pyrazinecarboxamide; and (c) contacting 3,6-difluoro-2-pyrazinecarboxamide with aqueous base to form 6-fluoro-3-hydroxypyrazine-2-carboxamide as depicted in FIG. 11. The preparation of 2,5-difluoropyrazine is described in more detail in Sections (I)(a) through (I)(c).

(a) Step (a)

Step (a) of the three step process encompasses contacting the 2,5-difluoropyrazine with palladium (0) catalyst in the presence of cyanogen bromide and an inorganic base to form 3,6-difluoro-2-pyrazinecarbonitrile.

A wide variety of Pd (0) catalysts may be used in Step (a) of the three step method. Non-limiting examples of the catalysts may be Pd(0) catalysts with various aryl phosphine ($Pd(Ph_3)_4$), alkyl phosphine, aryl alkyl phosphine ligands, or other ligands; Pd(0) precatalysts with various aryl phosphine ligands alkyl phosphine, aryl alkyl phosphine ligands, or other ligands; and various Pd(II) catalysts which are reduced in-situ to form Pd(0) catalysts. In an embodiment, the useful palladium catalyst is $Pd(Ph_3)_4$.

Numerous inorganic bases may be utilized in Step (a) besides. Non-limiting examples of these inorganic bases may be $Li_2CO_3$, $K_2CO_3$, $Na_2CO_3$, $MgCO_3$, or $BaCO_3$. In an embodiment, the useful base is $K_2CO_3$.

In general, the mole ratio of 2,5-difluoropyrazine to cyanogen bromide may range from about 1.0:1.0 to about 1.0:2.0. In various embodiments, the mole ratio of 2,5-difluoropyrazine to cyanogen bromide may range from about 1.0:1.0 to about 1.0:2.0, from about 1.0:1.0 to about 1.0:1.5, or from about 1.0:1.0 to about 1.0:1.3.

Generally, the mole ratio of 2,5-difluoropyrazine to Pd(0) catalyst may range from about 1.0:0.001 to about 1.0:0.1. In various embodiments, the mole ratio of 2,5-difluoropyrazine to Pd(0) catalyst may range from about 1.0:0.001 to about 1.0:0.1, from about 1.0:0.005 to about 1.0:0.08, or from about 1.0:0.01 to about 1.0:0.06.

In general, the mole ratio of 2,5-difluoropyrazine to inorganic base may range from about 1.0:2.0 to about 1.0:20.0. In various embodiments, the mole ratio of 2,5-difluoropyrazine to inorganic base may range from about 1.0:2.0 to about 1.0:20.0, from about 1.0:6.0 to about 1.0:15.0, or from about 1.0:8.0 to about 1.0:12.0.

Generally, a solvent is used in Step (a). A list of suitable solvents is described above in Section (I)(a). In one embodiment, the solvent useful in Step (d) is toluene.

Generally, the concentration of 2,5-difluoropyrazine in the solvent will range from about 0.05M to about 1.0M. In various embodiments, the concentration of 2,5-difluoropyrazine in the solvent may range from about 0.05M to about 1.0M, from about 0.08M to about 2.0M, or from about 0.01M to about 1.0M.

In general, the reaction of Step (a) will be conducted at a temperature that ranges from about 50° C. to about 120° C. depending on the solvent utilized. In various embodiments, the temperature of the reaction may range from about 50° C. to about 120° C., from about 80° C. to about 110° C., or from about 100° C. to about 110° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,5-difluoropyrazine. Typically, the amount 2,5-difluoropyrazine remaining in the reaction mixture at the end of the reaction may be less than about 10%, less than about 5%, or less than about 2%.

Suitable methods for purifying 3,6-difluoro-2-pyrazinecarbonitrile are described in the arts.

3,6-Difluoro-2-pyrazinecarbonitrile may have a yield of at least about 60%. In various embodiments, 3,6-difluoro-2-pyrazinecarbonitrile may have a yield of at least about 60%, at least about 65%, at least about 70%, at least about 75%, at least about 80%, at least about 85%, at least about 90%, at least about 95%, or at least about 99%.

(b) Step (b)

Step (b) of the three Step method comprises hydrolysis of the nitrile with concentrated HCl. Typically, the hydrolysis Step (b) may be conducted in the presence of a co-solvent, such as THF.

In general, the amount of concentrated HCl is used in excess as compared to the 3,6-difluoro-2-pyrazinecarbonitrile.

Generally, a solvent is used in Step (b). A list of suitable solvents is described above in Section (I)(a). In one embodiment, the solvent useful in Step (b) is THF.

Generally, the volume to weight ratio of the solvent to 3,6-difluoro-2-pyrazinecarbonitrile will range from about 0.5:1 to about 500:1. In various embodiments, the volume to weight ratio of the solvent to 3,6-difluoro-2-pyrazinecarbonitrile may range from about 0.5:1 to about 500:1, from about 2:1 to about 250:1, from about 5:1 to about 200:1, or from about 10:1 to about 100:1. In an embodiment, the volume to weight ratio of solvent to 3,6-difluoro-2-pyrazinecarbonitrile may range from about 20:1 to about 75:1.

In general, the reaction of Step (b) will be conducted at a temperature that ranges from about 25° C. to about 100° C. depending on the solvent utilized. In various embodiments, the temperature of the reaction may range from about 25° C. to about 100° C., from about 40° C. to about 80° C., or from about 50° C. to about 70° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3,6-difluoro-2-pyrazinecarbonitrile. Typically, the amount 3,6-difluoro-2-pyrazinecarbonitrile remaining in the reaction mixture at the end of the reaction may be less than about 10%, less than about 5%, or less than about 2%.

Suitable methods for purifying 3,6-difluoro-2-pyrazinecarboxamide are described in Section (I)(a).

3,6-Difluoro-2-pyrazinecarboxamide may have a yield of at least about 60%. In various embodiments, 3,6-difluoro-2-pyrazinecarbonitrile may have a yield of at least about 60%, at least about 65%, at least about 70%, at least about 75%, at least about 80%, at least about 85%, at least about 90%, at least about 95%, or at least about 99%.

(c) Step (c)

Step (c) of the three step process encompasses contacting the 3,6-difluoro-2-pyrazinecarboxamide with an aqueous base to form 6-fluoro-3-hydroxypyrazine-2-carboxamide. Suitable aqueous bases and conditions are described in more detail above in Section (IV)(c). In an embodiment, the aqueous base in sodium bicarbonate.

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 12:
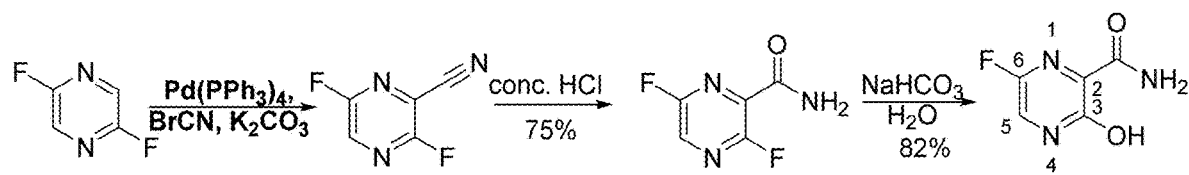
FIG. 12 is a chemical scheme for a preferred embodiment to prepare 6-fluoro-3-hydroxypyrazine-2-carboxamide according to FIG. 11.

In a preferred embodiment as shown in FIG. 12, the 2,5-diketopiperazine is contacted with PdPh$_4$ and K$_2$CO$_3$ to form 3,6-difluoro-2-pyrazinecarbonotrile; the 3,6-difluoro-2-pyrazinecarbonotrile is contacted with concentrated HCl to form 3,6-difluoro-2-pyrazinecarboxamide; and the 3,6-difluoro-2-pyrazinecarboxamide is contacted with aqueous sodium bicarbonate to form 6-fluoro-3-hydroxypyrazine-2-carboxamide in at least a 60% yield.

Figure 13:
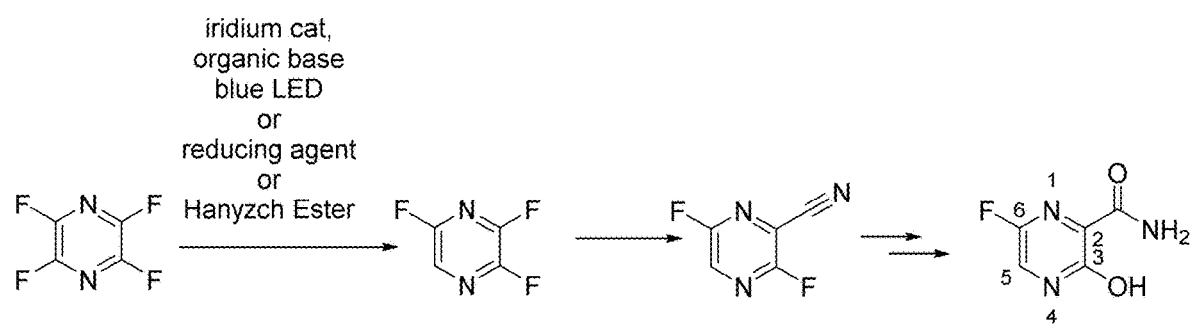
FIG. 13 is a chemical scheme for a method to prepare 6-fluoro-3-hydroxypyrazine-2-carboxamide.

(VII) Method Depicted in FIG. 13

One additional aspect of the present disclosure encompasses methods for the preparation of 6-fluoro-3-hydroxypyrazine-2-carboxamide. The method comprises: (a) contacting 2,3,5,6-tetrafluoropyrazine with an iridium catalyst, an organic base, and blue LEDs; a reducing agent; or a Hantzch ester to form 2,3,5-trifluoropyrazine; (b) contacting 2,3,5-trifluoropyrazine with an inorganic cyanide to form 3,6-difluoro-2-pyrazinecarbonitrile; (c) contacting 3,6-difluoro-2-pyrazinecarbonitrile with an aqueous acid to form 3,6-difluoro-2-pyrazinecarboxamide; and (d) contacting 3,6-difluoro-2-pyrazinecarboxamide with an aqueous base to form 6-fluoro-3-hydroxypyrazine-2-carboxamide as depicted in FIG. 13. Method for preparing 2,3,5,6-tetrafluoropyrazine are described in more detail above.

Method of contacting the 2,3,5,6-tetrafluoropyrazine with an iridium catalyst, an organic base, and blue LEDs are described in more detail in Section (II).

Method of contacting the 2,3,5,6-tetrafluoropyrazine with a reducing agent are described above in Section (I).

Method of contacting the 2,3,5,6-tetrafluoropyrazine with a Hantzch ester are described in more detail in Section (III).

Suitable methods for purifying 2,3,5-trifluoropyrazine are known in the art.

2,3,5-Trifluoropyrazine may have a yield of at least about 60%. In various embodiments, 2,3,5-trifluoropyrazine may have a yield of at least about 60%, at least about 65%, at least about 70%, at least about 75%, at least about 80%, at least about 85%, at least about 90%, at least about 95%, or at least about 99%.

(b) Step (b)

Step (b) of the four step method encompasses contacting the 2,3,5-trifluoropyrazine with an inorganic cyanide to form 3,6-difluoro-2-pyrazinecarbonitrile. Non-limiting examples of these inorganic cyanides may be sodium cyanide, potassium cyanide, lithium cyanide, cesium cyanide, copper (II) cyanide, and trialkylsilyl cyanides. In an embodiment, the inorganic cyanide may be sodium cyanide.

In general, the mole ratio of 2,3,5-trifluoropyrazine to inorganic cyanide may range from about 1.0:0.01 to about 1.0:1.0. In various embodiments, the mole ratio of 2,3,5-trifluoropyrazine to inorganic cyanide may range from about 1.0:0.01 to about 1.0:1.0, from about 1.0:0.1 to about 1.0:1.0, or from about 1.0:0.25 to about 1.0:0.75.

Generally, a solvent is used in Step (b). A list of suitable solvents is described above in Section (I)(a). In one embodiment, the solvent useful in Step (b) is 1,4-dioxane in water.

Generally, the concentration of 2,3,5-trifluoropyrazine in the solvent may range from about 0.1M to about 1.0M. In various embodiments, the concentration of 2,3,5-trifluoropyrazine in solvent may range from about 0.1M to about 1.0M, from about 0.25M to about 0.75M, or from 0.4M to about 0.6M.

In general, the reaction of Step (a) will be conducted at a temperature that ranges from about −25° C. to about 50° C. depending on the solvent utilized. In various embodiments, the temperature of the reaction may range from about −25° C. to about 50° C., from about −10° C. to about 30° C., or from about 0° C. to about 25° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,3,5-trifluoropyrazine. Typically, the amount 2,3,5-trifluoropyrazine remaining in the reaction mixture at the end of the reaction may be less than about 10%, less than about 5%, or less than about 2%.

Suitable methods for purifying 3,6-difluoro-2-pyrazinecarbonitrile are described above.

3,6-Difluoro-2-pyrazinecarbonitrile may have a yield of at least about 60%. In various embodiments, 3,6-difluoro-2-pyrazinecarbonitrile may have a yield of at least about 60%, at least about 65%, at least about 70%, at least about 75%, at least about 80%, at least about 85%, at least about 90%, at least about 95%, or at least about 99%.

(c) Step (c)

Step (c) of the four Step method comprising contacting the nitrile with concentrated HCl. Suitable methods are described in more detail above in Section (VI)(b).

(d) Step (d)

Step (d) of the four Step method is described in more detail above in Section (VI)(c).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 14:
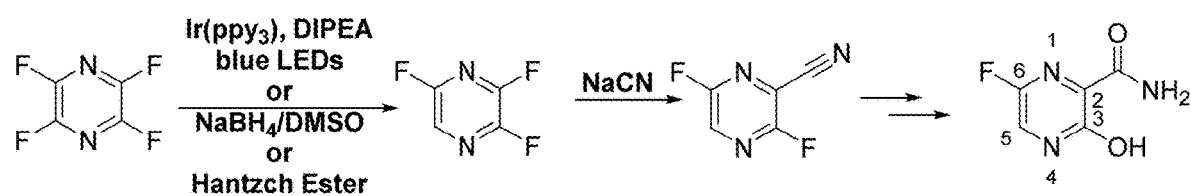
FIG. 14 is a chemical scheme for a preferred embodiment to prepare 6-fluoro-3-hydroxypyrazine-2-carboxamide according to FIG. 13.

In a preferred embodiment as shown in FIG. 14, the 2,3,5,6-tetrafluoropyrazine is contacted with an iridium catalyst comprises Ir(py)₃, diisopropylethylamine, and blue LEDs; sodium borohydride; or diethyl 1,4-dihydro-2,6-dimethyl-3,5-pyridinedicarboxylate to form 2,3,5-trifluoropyrazine; the 2,3,5-trifluoropyrazine is contacted with sodium cyanide to form 3,6-difluoro-2-pyrazinecarbonitrile; the 3,6-difluoro-2-pyrazinecarbonitrile is contacted with HCl to form 3,6-difluoro-2-pyrazinecarboxamide; and 3,6-difluoro-2-pyrazinecarboxamide is contacted with aqueous sodium bicarbonate to form 6-fluoro-3-hydroxypyrazine-2-carboxamide in at least a 60% yield.

Figure 15:
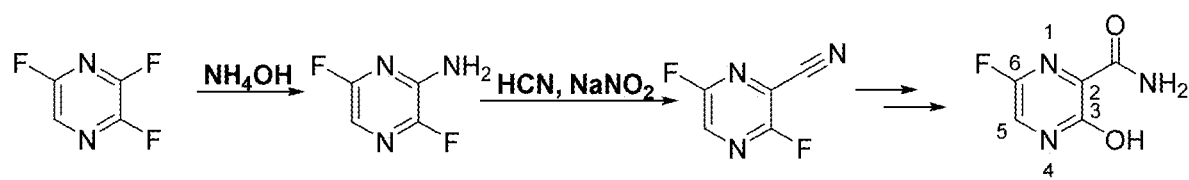
FIG. 15 is a chemical scheme for a method to prepare 6-fluoro-3-hydroxypyrazine-2-carboxamide.

(VIII) Method Depicted in FIG. 15

One additional aspect of the present disclosure encompasses methods for the preparation of 6-fluoro-3-hydroxypyrazine-2-carboxamide. The method comprises: (a) contacting 2,3,5-trifluoropyrazine with ammonium hydroxide to form 3,6-difluoro-2-pyrazinamine; (b) contacting 3,6-difluoro-2-pyrazinamine with hydrogen cyanide, sodium nitrite, and benzoic acid to 3,6-difluoro-2-pyrazinecarbonitrile; (c) contacting 3,6-difluoro-2-pyrazinecarbonitrile with an aqueous acid to form 3,6-difluoro-2-pyrazinecarboxamide; and (d) contacting 3,6-difluoro-2-pyrazinecarboxamide with aqueous base to form 6-fluoro-3-hydroxypyrazine-2-carboxamide as depicted in FIG. 15. Method for preparing 2,3,5-trifluoropyrazine are described in more detail above.

(a) Step (a).

Step (a) of the three Step method comprises contacting 2,3,5-trifluoropyrazine with ammonium hydroxide to form 3,6-difluoro-2-pyrazinamine.

In general, the mole ratio of 2,3,5-trifluoropyrazine to ammonium hydroxide in the quench may range from about 1.0:2.0 to about 1.0:100.0. In various embodiments, the mole ratio of 2,3,5-trifluoropyrazine to ammonium hydroxide in the quench may range from about 1.0:2.0 to about 1.0:100.0, from about 1.0:5.0 to about 1.0:80.0, or from about 1.0:10.0 to about 1.0:50.0.

Step (a) of the three step process may be conducted in the presence of a solvent. Suitable solvents are described above in Section (I)(a). In one embodiment, the solvent useful in the Step (a) is methanol.

In general, the concentration of 2,3,5-trifluoropyrazine in the solvent may range from about 0.01M to about 1.0M. In various embodiments, the concentration of 2,3,5-trifluoropyrazine in the solvent may range from about 0.01M to about 1.0M, from about 0.05M to about 0.5M, from about 0.08M to about 0.12M.

In general, the reaction of Step (a) will be conducted at a temperature that ranges from about 0° C. to about 100° C. depending on the solvent utilized. In various embodiments, the temperature of the reaction may range from about 0° C. to about 100° C., from about 25° C. to about 80° C., or from about 30° C. to about 60° C. In one embodiment, the reaction temperature of Step (a) may be about room temperature. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2,3,5-trifluoropyrazine. Typically, the amount 2,3,5-trifluoropyrazine remaining in the reaction mixture at the end of the reaction may be less than about 10%, less than about 5%, or less than about 2%.

Suitable methods for purifying 2,3,5-trifluoropyrazine are described in Section (I)(a).

3,6-Difluoro-2-pyrazinamine may have a yield of at least about 60%. In various embodiments, 3,6-difluoro-2-pyrazinamine may have a yield of at least about 60%, at least about 65%, at least about 70%, at least about 75%, at least about 80%, at least about 85%, at least about 90%, at least about 95%, or at least about 99%.

(b) Step (b)

Step (b) of the four step method encompasses contacting the 3,6-difluoro-2-pyrazinamine with sodium nitrite, hydrogen cyanide, and benzoic acid to form 3,6-difluoro-2-pyrazinecarbonitrile.

In general, the mole ratio of 3,6-difluoro-2-pyrazinamine to sodium nitrite may range from about 1.0:1.0 to about 1.0:5.0. In various embodiments, the mole ratio of 3,6-difluoro-2-pyrazinamine to sodium nitrite may range from about 1.0:1.0 to about 1.0:5.0, from about 1.0:1.5 to about 1.0:4.5, or from about 1.0:2.0 to about 1.0:4.0.

Generally, the mole ratio of 3,6-difluoro-2-pyrazinamine to HCN may range from about 1.0:1.0 to about 1.0:2.0. In various embodiments, the mole ratio of 3,6-difluoro-2-pyrazinamine to HCN may range from about 1.0:1.0 to about 1.0:2.0, from about 1.0:1.2 to about 1.0:1.8, or from about 1.0:1.4 to about 1.0:1.6.

In general, the mole ratio of 3,6-difluoro-2-pyrazinamine to benzoic acid may range from about 1.0:1.0 to about 1.0:5.0. In various embodiments, the mole ratio of 3,6-difluoro-2-pyrazinamine to benzoic acid may range from about 1.0:1.0 to about 1.0:5.0, from about 1.0:1.5 to about 1.0:4.5, or from about 1.0:2.0 to about 1.0:4.0.

Generally, a solvent is used in Step (b). A list of suitable solvents is described above in Section (I)(a). In one embodiment, the appropriate solvent comprises DMSO and water.

Generally, the volume to weight ratio of solvent to 3,6-difluoro-2-pyrazinamine will range from about 0.5:1 to about 500:1. In various embodiments, the volume to weight ratio of the solvent to 3,6-difluoro-2-pyrazinamine may range from about 0.5:1 to about 500:1, from about 2:1 to about 250:1, from about 5:1 to about 200:1, or from about 10:1 to about 100:1. In an embodiment, the volume to weight ratio of DMSO and water to 3,6-difluoro-2-pyrazinamine may range from about 20:1 to about 75:1.

In general, the reaction of Step (b) will be conducted at a temperature that ranges from about 0° C. to about 100° C. depending on the solvent utilized. In various embodiments, the temperature of the reaction may range from about 0° C. to about 100° C., from about 20° C. to about 80° C., or from about 40° C. to about 60° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3,6-difluoro-2-pyrazinamine. Typically, the amount of 3,6-difluoro-2-pyrazinamine remaining in the reaction mixture at the end of the reaction may be less than about 10%, less than about 5%, or less than about 2%.

Suitable methods for purifying 3,6-difluoro-2-pyrazinecarbonitrile are described above.

3,6-Difluoro-2-pyrazinecarbonitrile may have a yield of at least about 60%. In various embodiments, 3,6-difluoro-2-pyrazinecarbonitrile may have a yield of at least about 60%, at least about 65%, at least about 70%, at least about 75%, at least about 80%, at least about 85%, at least about 90%, at least about 95%, or at least about 99%.

(c) Step (c)

Step (c) of the four step method comprising contacting the nitrile with concentrated HCl. Suitable methods are described in more detail above in Section (VI)(b).

(d) Step (d)

Step (d) of the four step method is described in more detail above in Section (VI)(c).

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 16:
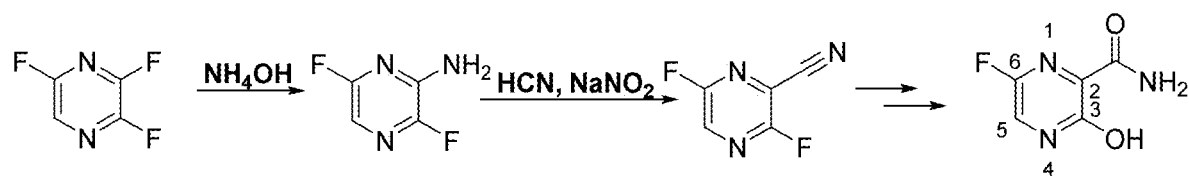
FIG. 16 is a chemical scheme for a preferred embodiment to prepare 6-fluoro-3-hydroxypyrazine-2-carboxamide according to FIG. 15.

In a preferred embodiment as shown in FIG. 16, the 2,3,5-trifluoropyrazine is contacted with ammonium hydroxide to form 3,6-difluoro-2-pyrazinamine; the 3,6-difluoro-2-pyrazinamine is contacted with hydrogen cyanide, sodium nitrite, and benzoic acid to form 3,6-difluoro-2-pyrazinecarbonitrile; the 3,6-difluoro-2-pyrazinecarbonitrile is contacted with HCl to form 3,6-difluoro-2-pyrazinecarboxamide; and the 6-difluoro-2-pyrazinecarboxamide is contacted with aqueous sodium bicarbonate to form 6-fluoro-3-hydroxypyrazine-2-carboxamide in at least a 60% yield.

Figure 17:
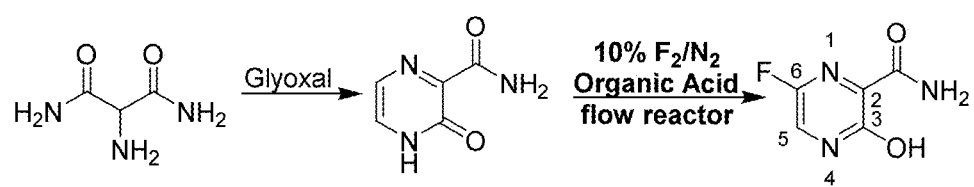
FIG. 17 is a chemical scheme for a method to prepare 6-fluoro-3-hydroxypyrazine-2-carboxamide.

(IX) Method Depicted in FIG. 17

One additional aspect of the present disclosure encompasses methods for the preparation of 6-fluoro-3-hydroxypyrazine-2-carboxamide. The method comprises: (a) contacting 2-am inopropanediam ide with glyoxal in the presence of a base to form 3-hydroxy-2-pyrazinecarboxamide; and (b) contacting 3-hydroxy-2-pyrazinecarboxamide with 10% $F_2/1 N_2$ in the presence of an organic acid in a flow reactor to form 6-fluoro-3-hydroxypyrazine-2-carboxamide. as depicted in FIG. 17.

(a) Step (a).

Step (a) of the two step method comprises contacting 2-aminopropanediamide with glyoxal in the presence of an inorganic base to form 3-hydroxy-2-pyrazinecarboxamide.

A wide variety of inorganic bases may be used in this method step. Non-limiting examples of these inorganic bases may be LiOH, NaOH, KOH, $Ca(OH)_2$, $Ba(OH)_2$, or combinations thereof. In one embodiment, the base useful in this step is NaOH.

In general, the mole ratio of 2-aminopropanediamide to base may range from about 1.0:0.5 to about 1.0:2.0. In various embodiments, the mole ratio of 2-aminopropanediamide to base may range from about 1.0:0.5 to about 1.0:2.0, from about 1.0:0.6 to about 1.0:1.5, or from about 1.0:0.8 to about 1.0:1.2.

Generally, the mole ratio of 2-aminopropanediamide to glyoxal may range from about 1.0:2.0 to about 1.0:20.0. In various embodiments, the mole ratio of 2-aminopropanediamide to glyoxal may range from about 1.0:2.0 to about 1.0:20.0, from about 1.0:6.0 to about 1.0:15.0, or from about 1.0:9.0 to about 1.0:10.0.

A solvent may be used in Step (a). Suitable solvent are described above in Section (IA)(a). In one embodiment, the solvent useful in Step (a) is water.

Generally, the concentration of the 2-aminopropanediamide in the solvent may range from 0.5M to about 2.0M. In various embodiments, the concentration of the 2-am inopropanediam ide in the solvent may range from 0.5M to about 2.0M, from about 0.6M to about 1.5M, or from about 0.8M to about 1.2M.

In general, the reaction of Step (a) will be conducted at a temperature that ranges from about −50° C. to about 50° C. depending on the solvent utilized. In various embodiments, the temperature of the reaction may range from about −50° C. to about 50° C., from about −25° C. to about 25° C., or from about −20° C. to about 10° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 2-am inopropanediam ide. Typically, the amount 2-am inopropanediam ide remaining in the reaction mixture at the end of the reaction may be less than about 10%, less than about 5%, or less than about 2%.

Suitable methods for purifying 3-hydroxy-2-pyrazinecarboxamide are known in the art.

3-Hydroxy-2-pyrazinecarboxamide may have a yield of at least about 60%. In various embodiments, 3,6-difluoro-2-pyrazinamine may have a yield of at least about 60%, at least about 65%, at least about 70%, at least about 75%, at least about 80%, at least about 85%, at least about 90%, at least about 95%, or at least about 99%.

(b) Step (b)

Step (b) of the two step method encompasses contacting the 3-hydroxy-2-pyrazinecarboxamide with a mixture of fluorine gas and nitrogen gas in organic acid in a flow reactor to form 6-fluoro-3-hydroxypyrazine-2-carboxamide. In one embodiment, the useful concentration of fluorine in nitrogen gas is about 10%.

In general, the mole ratio of 3,6-difluoro-2-pyrazinamine to 10% $F_2/N_2$ may range from about 1.0:1.0 to about 1.0:2.0. In various embodiments, the mole ratio of 3,6-difluoro-2- pyrazinamine to 10% $F_2/N_2$ may range from about 1.0:1.0 to about 1.0:2.0, from about 1.0:1.0 to about 1.0:1.5, or from about 1.0:1.0 to about 1.0:1.3.

A wide variety of organic acids may be used in Step (b). Non-limiting examples of organic acids may be formic acid, acetic acid, or propionic acid. In one embodiment, the organic acid is formic acid.

Generally, a solvent is used in Step (b). A list of suitable solvents is described above in Section (I)(a).

Generally, the concentration of 3-hydroxy-2-pyrazinecarboxamide in the organic acid may range from about 0.5M to about 2.0M. In various embodiments, the concentration of 3-hydroxy-2-pyrazinecarboxamide in organic acid may range from about 0.5M to about 2.0M, from about 0.8M to about 1.5M, or from about 0.9M to about 1.1M.

In general, the reaction of Step (b) will be conducted at a temperature that ranges from about 0° C. to about 100° C. depending on the solvent utilized. In various embodiments, the temperature of the reaction may range from about 0° C. to about 100° C., from about 20° C. to about 80° C., or from about 40° C. to about 60° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3-hydroxy-2-pyrazinecarboxamide. Typically, the amount of 3-hydroxy-2-pyrazinecarboxamide remaining in the reaction mixture at the end of the reaction may be less than about 10%, less than about 5%, or less than about 2%.

Suitable methods for purifying 6-fluoro-3-hydroxypyrazine-2-carboxamide are described in the art.

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 18:
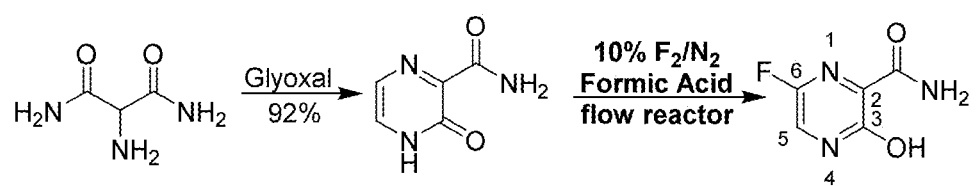
FIG. 18 is a chemical scheme for a preferred embodiment to prepare 6-fluoro-3-hydroxypyrazine-2-carboxamide according to FIG. 17.

In a preferred embodiment as shown in FIG. 18, the 2-aminopropanediamide is contacted with glyoxal and NaOH to form 3-hydroxy-2-pyrazinecarboxamide; and the 3-hydroxy-2-pyrazinecarboxamide is contacted with 10% $F_2/N_2$ and formic acid in a flow reactor to form 6-fluoro-3-hydroxypyrazine-2-carboxamide in at least a 60% yield.

Figure 19:
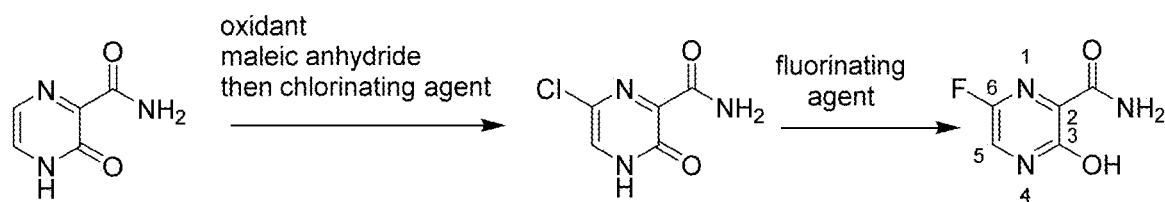
FIG. 19 is a chemical scheme for a method to prepare 6-fluoro-3-hydroxypyrazine-2-carboxamide.

(X) Method Depicted in FIG. 19

One additional aspect of the present disclosure encompasses methods for the preparation of 6-fluoro-3-hydroxypyrazine-2-carboxamide. The method comprises: (a) contacting 3-hydroxy-2-pyrazinecarboxamide with an oxidant and maleic anhydride followed by a chlorinating agent to form 6-chloro-3,4-dihydro-3-oxo-2-pyrazinecarboxamide; and (b) contacting 6-chloro-3,4-dihydro-3-oxo-2-pyrazinecarboxamide with a fluorinating agent to form 6-fluoro-3-hydroxypyrazine-2-carboxamide as depicted in FIG. 19.

(a) Step (a).

Step (a) of the two Step method comprises contacting 3-hydroxy-2-pyrazinecarboxamide with maleic anhydride in the presence of an oxidant. After the pyrazine N-oxide is formed, the pyrazine N-oxide is contacted with chlorinating agent to form 6-chloro-3,4-dihydro-3-oxo-2-pyrazinecarboxamide. Methods of preparing 3-hydroxy-2-pyrazinecarboxamide are described above in Section (IX)(a).

Numerous oxidants can be utilized. Non-limiting examples of these oxidants may be $H_2O_2$, $MeReO_3$ with $H_2O_2$, $HOReO_3$ with $(Me_3SiO)_2$, dimethyldioxirane, mCPBA, peracetic acid, acetic acid and urea hydroperoxide, and Caro's reagent. In an embodiment, the oxidant in Step (a) is $H_2O_2$.

A wide variety of oxidants can be used. Non-limiting examples of these reagents may be phosphorus oxychloride, phosphorus pentachloride, phosgene, trichloroacetyl chloride, methanesulfonyl chloride, benzenesulfonyl chloride, and p-toluenesulfonyl chloride. In an embodiment, the chlorinating agent is phosphorus oxychloride.

In general, the mole ratio of 3-hydroxy-2-pyrazinecarboxamide to maleic anhydride may range from about 1.0:2.0 to about 1.0:30.0. In various embodiments, the mole ratio of 3-hydroxy-2-pyrazinecarboxamide to maleic anhydride may range from about 1.0:2.0 to about 1.0:30.0, from about 1.0:6.0 to about 1.0:25.0, or from about 1.0:8.0 to about 1.0:12.0.

Generally, the mole ratio of 3-hydroxy-2-pyrazinecarboxamide to the oxidant may range from about 1.0:2.0 to about 1.0:30.0. In various embodiments, the mole ratio of 3-hydroxy-2-pyrazinecarboxamide to the oxidant may range from about 1.0:2.0 to about 1.0:30.0, from about 1.0:6.0 to about 1.0:25.0, or from about 1.0:8.0 to about 1.0:12.0.

In general, the mole ratio of 3-hydroxy-2-pyrazinecarboxamide to the chlorinating agent may range from about 1.0:0.5 to about 1.0:3.0. In various embodiments, the mole ratio of 3-hydroxy-2-pyrazinecarboxamide to the chlorinating agent may range from about 1.0:0.5 to about 1.0:3.0, from about 1.0:0.8 to about 1.0:2.8, or from about 1.0:1.5 to about 1.0:2.5.

A solvent may be used in Step (a). Suitable solvent are described above in Section (I)(A)(a). In one embodiment, the suitable solvent used in Step (a) is dichloromethane.

Generally, the concentration of 3-hydroxy-2-pyrazinecarboxamide in the solvent will range from about 0.05M to about 1.0M. In various embodiments, concentration of 3-hydroxy-2-pyrazinecarboxamide in the solvent will range from about 0.05M to about 1.0M, from about 0.1M to about 0.5M, or from about 0.1M to about 0.3M.

In general, the reaction of Step (a) will be conducted at a temperature that ranges from about 20° C. to about 100° C. depending on the solvent utilized. In various embodiments, the temperature of the reaction may range from about 20° C. to about 100° C., from about 30° C. to about 60° C., or from about 40° C. to about 50° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 3-hydroxy-2-pyrazinecarboxamide. Typically, the amount 3-hydroxy-2-pyrazinecarboxamide remaining in the reaction mixture at the end of the reaction may be less than about 10%, less than about 5%, or less than about 2%.

Suitable methods for purifying 6-chloro-3,4-dihydro-3-oxo-2-pyrazinecarboxamide are known in the art.

6-Chloro-3,4-dihydro-3-oxo-2-pyrazinecarboxamide may have a yield of at least about 60%. In various embodiments, 6-chloro-3,4-dihydro-3-oxo-2-pyrazinecarboxamide may have a yield of at least about 60%, at least about 65%, at least about 70%, at least about 75%, at least about 80%, at least about 85%, at least about 90%, at least about 95%, or at least about 99%.

(b) Step (b)

As discussed above, Step (b) of the two step method involves contacting 6-chloro-3,4-dihydro-3-oxo-2-pyrazinecarboxamide with a fluorinating agent to form 6-fluoro-3-hydroxypyrazine-2-carboxamide.

Step (b) is described in more detail above in Section (I).

In general, the reaction of Step (b) will be conducted at a temperature that ranges from about 80° C. to about 160° C. depending on the solvent utilized. In various embodiments, the temperature of the reaction may range from about 80° C. to about 160° C., from about 100° C. to about 140° C., or from about 110° C. to about 130° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 24 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours. In an embodiment, the reaction may be allowed to proceed for about 10 hours to about 16 hours. In this context, a "completed reaction" generally means that the reaction mixture contains a significantly diminished amount of 6-chloro-3,4-dihydro-3-oxo-2-pyrazinecarboxamide. Typically, the amount 6-chloro-3,4-dihydro-3-oxo-2-pyrazinecarboxamide remaining in the reaction mixture at the end of the reaction may be less than about 10%, less than about 5%, or less than about 2%.

6-Fluoro-3-hydroxypyrazine-2-carboxamide may have a yield of at least about 60%. In various embodiments, 6-fluoro-3-hydroxypyrazine-2-carboxamide may have a yield of at least about 60%, at least about 65%, at least about 70%, at least about 75%, at least about 80%, at least about 85%, at least about 90%, at least about 95%, or at least about 99%.

Preferred Embodiment

Figure 20:
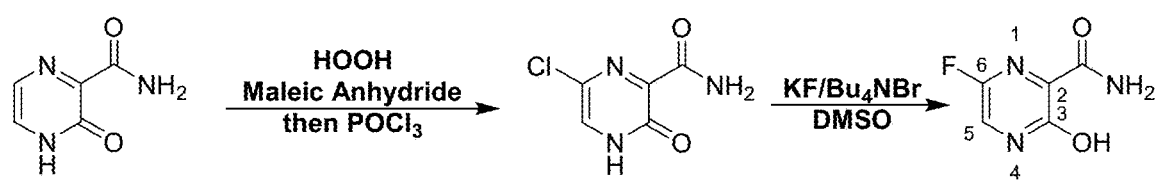
FIG. 20 is a chemical scheme for a preferred embodiment to prepare 6-fluoro-3-hydroxypyrazine-2-carboxamide according to FIG. 19.

In a preferred embodiment as shown in FIG. 20, the 23-hydroxy-2-pyrazinecarboxamide is contacted with hydrogen peroxide and maleic anhydride followed by phosphorus oxy chloride to form 6-chloro-3,4-dihydro-3-oxo-2-pyrazinecarboxamide; and the 6-chloro-3,4-dihydro-3-oxo-2-pyrazinecarboxamide is contacted with potassium fluoride and tetrabutylammonium bromide to form 6-fluoro-3-hydroxypyrazine-2-carboxamide in at least a 60% yield.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described methods without departing from the scope of the invention, it is intended that all matter contained in the above description and in the examples given below, shall be interpreted as illustrative and not in a limiting sense.

EXAMPLE 1

Preparation of 2,3,5,6-tetrachloropyrazine

Into a round bottom flask was added 2,5-diketopiperazine. To the reaction was added phosphorus oxychloride and phosphorus pentachloride. After stirring for a few minutes, chlorine gas was added. The reaction was warmed to 120° C. After stirring for a period of 1 hour, the reaction was deemed complete. The reaction was worked up and the 2,3,5,6-tetrachloropyrazine was isolated in 92% yield.

EXAMPLE 2

Preparation of 2,3,5,6-tetrafluoropyrazine

Into a round bottom flask was added 2,3,5,6-tetrachloropyrazine and DMSO. To the reaction was added potassium fluoride (6 equiv) and tetrabutylammonium bromide (1.2 equiv). The reaction was warmed to 65° C. and stirred for 4 hours where the reaction was deemed complete. The reaction was worked up and the 2,3,5,6-tetrafluoropyrazine was isolated.

EXAMPLE 3

Preparation of 2,5-difluoropyrazine

Into a round bottom flask may be added 2,3,5,6-tetrafluoropyrazine and DMSO. To the reaction was added sodium borohydride (2.2 equiv). The reaction was stirred at room temperature for 35 minutes where the reaction was complete. The reaction was worked up and the 2,5-difluoropyrazine was isolated.

EXAMPLE 4

Preparation of 6-fluoro-3-hydroxypyrazine

Into a round bottom flask was added 2,5-difluoropyrazine and THF. The reaction was cooled to 0° C. A solution of LDA (1.1 equiv) was added. After 1 hour of stirring, trimethylsilyl isocyanate (1.15 equiv) may be added. The reaction was warmed to room temperature. To the reaction was added 1,4-dioxane and 9-10 equivalents of a 0.5M solution of NaHCO$_3$. The reaction was warmed to 60° C.

and stirred until complete. The reaction was cooled to room temperature and worked-up. The 6-fluoro-3-hydroxypyrazine was isolated.

EXAMPLE 5

Preparation of 2,5-difluoropyrazine

Into a round bottom flask was be added 2,3,5,6-tetrafluoroopyrazine and $CH_3CN$. To the reaction was added diisopropylethylamine (4 equiv). Then, a catalytic amount of $Ir(ppy)_3$ (0.25 mole %) is added. Blue LEDs are irradiated into the reaction. The reaction was stirred at room temperature then warmed to 35° C. until complete. The reaction was worked up and the 2,5-difluoropyrazine was isolated.

EXAMPLE 5

Preparation of 2,5-difluoropyrazine

Into a round bottom flask was added 2,3,5,6-tetrafluoroopyrazine and DMF. To the reaction, the Hantzch ester (1.2 equiv) was added. After stirring to provide homogeneity, the reaction may be illuminated with 405 nm light for 6-8 hours. The reaction was complete. The reaction was worked up and the 2,5-difluoropyrazine was isolated.

EXAMPLE 6

Preparation of 6-fluoro-3-hydroxypyrazine-2-carboxamide

Into a round bottom flask was added 2,5-difluoropyrazine and THF. The reaction was cooled to 0° C. Lithium diisopropylamide (1.1 equiv) was added and for 1 hour. Then, dimethylcarbonate (1.15 equiv) was added and the reaction was stirred for 4 hours. After stirring for 4 hours, ammonium hydroxide in methanol was added. The reaction stirred for 6 hours. To the reaction was added saturated sodium bicarbonate and the reaction may be stirred overnight at room temperature. To the reaction was added 1,4-dioxane and 9-10 equivalents of a 0.5M aqueous solution of $NaHCO_3$. The reaction was warmed to 60° C. and stirred until complete. The reaction was cooled to room temperature and worked-up. The 6-fluoro-3-hydroxypyrazine-2-carboxamide was isolated in 82% yield.

EXAMPLE 7

Preparation of 6-fluoro-3-hydroxypyrazine-2-carboxamide

Into a round bottom flask was added 2,5-difluoropyrazine and THF. The reaction was cooled to 0° C. Lithium diisopropylamide (1.1 equiv) was added and for 1 hour. Then, gaseous carbon dioxide was added subsurface and the reaction was warmed to room temperature. After stirring for 6 hours, thionyl chloride (1.1 equiv) was added and the reaction was warmed to 80° C. After stirring for 8 hours at room temperature, the reaction was cooled to 0° C. and methanol/ammonium hydroxide was added (10 equiv). The reaction was stirred overnight at room temperature and worked up yielding 6-fluoro-3-hydroxypyrazine-2-carboxamide.

EXAMPLE 8

Preparation of 6-fluoro-3-hydroxypyrazine-2-carboxamide

Into a round bottom flask was added 2,5-difluoropyrazine and toluene. To the reaction was added potassium carbonate (10.0 equiv) followed by a catalytic amount of $Pd(Ph_3)_4$ (5.0 mole %). The reaction was warmed to 75° C. and the cyanogen bromide (1.2 equiv) was added. The reaction was warmed to reflux. After stirring for 6 hours, the reaction was complete and the 3,6-difluoro-2-pyrazinecarbonitrile was isolated.

The 3,6-difluoro-2-pyrazinecarbonitrile was dissolved in THF and concentrated HCl added dropwise. After stirring at room temperature for 24 hours, the 6-fluoro-3-hydroxypyrazine-2-carboxamide was isolated in 75% yield.

EXAMPLE 9

Preparation of 3,6-difluoro-2-pyrazinecarbonitrile

Into a round bottom flask was added 2-am inopropanediamide, glyoxal, and water. The reaction was cooled to −10° C. and NaOH (1.0 equiv) was added. After the addition was complete. The reaction was warmed to room temperature. After stirring for 40 minutes, the reaction was complete. The reaction was worked up and the 6-fluoro-3-hydroxypyrazine-2-carboxamide was isolated in a 92% yield.

EXAMPLE 10

Preparation of 6-fluoro-3-hydroxypyrazine-2-carboxamide

Into a flow reactor was added 3-hydroxy-2-pyrazinecarboxamide and formic acid to achieve a concentration of 1M. Into the flow reactor was added 10% $F_2/N_2$ gas (1.2 equiv). After 1 hour, the reaction was complete and the 6-fluoro-3-hydroxypyrazine-2-carboxamide was isolated.

EXAMPLE 11

Preparation of 6-fluoro-3-hydroxypyrazine-2-carboxamide

Into a round bottom was added 3-hydroxy-2-pyrazinecarboxamide and DCM.

Into a round bottom flask may be added 6-fluoro-3-hydroxypyrazine-2-carboxamide was isolated after work-up from the reaction.

REFERENCES (1) Cai, Q.; Yang, M.; Liu, D.; Chen, J.; Shu, D.; Xia, J.; Liao, X.; Gu, Y.; Cai, Q.; Yang, Y.; Shen, C.; Li, X.; Peng, L.; Huang, D.; Zhang, J.; Zhang, S.; Wang, F.; Liu, J.; Chen, L.; Chen, S.; Wang, Z.; Zhang, Z.; Cao, R.; Zhong, W.; Liu, Y.; Liu, L. TEMPORARY REMOVAL: Experimental Treatment with Favipiravir for COVID-19: An Open-Label Control Study. *Engineering* 2020.

(2) Dong, L.; Hu, S.; Gao, J. Discovering drugs to treat coronavirus disease 2019 (COVID-19). *Drug discoveries & therapeutics* 2020, 14, 58.

(3) Chen, C.; Zhang, Y.; Huang, J.; Yin, P.; Cheng, Z.; Wu, J.; Chen, S.; Zhang, Y.; Chen, B.; Lu, M.; Luo, Y.; Ju, L.; Zhang, J.; Wang, X. Favipiravir versus Arbidol for COVID-19: A Randomized Clinical Trial. 2020, 2020.03.17.20037432.

(4) Furuta, Y.; Gowen, B. B.; Takahashi, K.; Shiraki, K.; Smee, D. F.; Barnard, D. L. Favipiravir (T-705), a novel viral RNA polymerase inhibitor. *Antiviral Research* 2013, 100, 446.

(5) Furuta, Y.; Takahashi, K.; Fukuda, Y.; Kuno, M.; Kamiyama, T.; Kozaki, K.; Nomura, N.; Egawa, H.; Minami, S.; Watanabe, Y.; Narita, H.; Shiraki, K. In Vitro and In Vivo Activities of Anti-Influenza Virus Compound T-705. 2002, 46, 977.

(6) Furuta, Y.; Takahashi, K.; Shiraki, K.; Sakamoto, K.; Smee, D. F.; Barnard, D. L.; Gowen, B. B.; Julander, J. G.; Morrey, J. D. T-705 (favipiravir) and related compounds: Novel broad-spectrum inhibitors of RNA viral infections. *Antiviral Research* 2009, 82, 95.

(7) Jin, Z.; Tucker, K.; Lin, X.; Kao, C. C.; Shaw, K.; Tan, H.; Symons, J.; Behera, I.; Rajwanshi, V. K.; Dyatkina, N.; Wang, G.; Beigelman, L.; Deval, J. Biochemical Evaluation of the Inhibition Properties of Favipiravir and 2'-<em>C</em>-Methyl-Cytidine Triphosphates against Human and Mouse Norovirus RNA Polymerases. 2015, 59, 7504.

What is claimed is:

1. A method for preparing 6-fluoro-3-hydroxypyrazine-2-carboxamide, the method comprising:
    (a) contacting 2,5-diketopiperazine with a chlorinating agent or a mixture of two or more chlorinating agents to form 2,3,5,6-tetrachloroppyrazine;
    (b) contacting 2,3,5,6-tetrachloropyrazine with fluorinating agent to form 2,3,5,6-tetrafluoropyrazine;
    (c) contacting 2,3,5,6-tetrafluoropyrazine with a reducing agent to form 2,5-difluoropyrazine; and
    (d) contacting 2,5-difluoropyrazine with an organic base and a trisubstitutedsilyl isocyanate to form 6-fluoro-3-hydroxypyrazine-2-carboxamide.

2. The method of claim 1, wherein the chlorinating agent or the mixture of two or more chlorinating agents comprise phosphorus oxychloride, phosphorus pentachloride, and chlorine gas; the fluorinating agent comprises potassium fluoride and tetrabutylammonium bromide; the reducing agent comprises sodium borohydride; the bases comprises lithium diisopropylamide; and the trisubstitutedsilyl isocyanate comprises trimethylsilyl isocyanate.

3. A method for preparing 6-fluoro-3-hydroxypyrazine-2-carboxamide, the method comprising:
    (a) contacting 2,5-diketopiperazine with a chlorinating agent or a mixture of two or more chlorinating agents to form 2,3,5,6-tetrachloropyrazine;
    (b) contacting 2,3,5,6-tetrachloropyrazine with a fluorinating agent in the presence of a solvent to form 2,3,5,6-tetrafluoropyrazine;
    (c) contacting 2,3,5,6-tetrafluoropyrazine with aa iridium catalyst, an organic base, and blue LEDS to form 2,5-difluoropiperazine; and
    (d) contacting 2,5-difluoropyrazine with a chlorinating agent or a mixture of two or more chlorinating agents to form 6-fluoro-3-hydroxypyrazine-2-carboxamide.

4. The method of claim 3, wherein the chlorinating agent or the mixture of two or more chlorinating agents comprise phosphorus oxychloride, phosphorus pentachloride, and chlorine gas; the fluorinating agent comprises potassium fluoride and tetrabutylammonium bromide; the iridium catalyst comprises Ir(py)$_3$; the organic base comprises diisopropylethylamine; and the trisubstitutedsilyl isocyanate comprises trimethylsilyl isocyanate.

5. A method for preparing 6-fluoro-3-hydroxypyrazine-2-carboxamide, the method comprising:
    (a) contacting 2,5-diketopiperazine with a chlorinating agent or the mixture of two or more chlorinating agents to form 2,3,5,6-tetrachloropyrazine;
    (b) contacting 2,3,5,6-tetrachloropyrazine with a fluorinating agent to form 2,3,5,6-tetrafluoropyrazine;
    (c) contacting 2,3,5,6-tetrafluoropyrazine with a Hantzch Ester in the presence of 405 nm light to form 2,5-difluoropyrazine; and
    (d) contacting 2,5-difluoropyrazine with a base and a trisubstitutedsilyl isocyanate to form 6-fluoro-3-hydroxypyrazine-2-carboxamide.

6. The method of claim 5, wherein the chlorinating agent or the mixture of two or more chlorinating agents comprise phosphorus oxychloride, phosphorus pentachloride, and chlorine gas; the fluorinating agent comprises potassium fluoride and tetrabutylammonium bromide; the Hantzch Ester comprises diethyl 1,4-dihydro-2,6-dimethyl-3,5-pyridinedicarboxylate; the bases comprises lithium diisopropylamide; and the trisubstitutedsilyl isocyanate comprises trimethylsilyl isocyanate.

* * * * *